(12) United States Patent
Tedder et al.

(10) Patent No.: US 10,017,739 B2
(45) Date of Patent: Jul. 10, 2018

(54) METHODS OF EXPANDING AND ASSESSING B CELLS AND USING EXPANDED B CELLS TO TREAT DISEASE

(71) Applicant: DUKE UNIVERSITY, Durham, NC (US)

(72) Inventors: Thomas F. Tedder, Durham, NC (US); Ayumi Yoshizaki, Durham, NC (US); Tomomitsu Miyagaki, Durham, NC (US); Evgueni Kountikov, Durham, NC (US); Jonathan C. Poe, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 13/795,889

(22) Filed: Mar. 12, 2013

(65) Prior Publication Data

US 2014/0065118 A1 Mar. 6, 2014

Related U.S. Application Data

(60) Provisional application No. 61/707,256, filed on Sep. 28, 2012, provisional application No. 61/697,663, filed on Sep. 6, 2012.

(51) Int. Cl.
| | |
|---|---|
| *C12N 5/02* | (2006.01) |
| *C12N 5/00* | (2006.01) |
| *C12N 5/0781* | (2010.01) |
| *A61K 35/17* | (2015.01) |

(52) U.S. Cl.
CPC ............ *C12N 5/0635* (2013.01); *A61K 35/17* (2013.01); *C12N 2501/15* (2013.01); *C12N 2501/231* (2013.01); *C12N 2501/2304* (2013.01); *C12N 2501/2306* (2013.01); *C12N 2501/2312* (2013.01); *C12N 2501/2321* (2013.01); *C12N 2501/24* (2013.01); *C12N 2501/52* (2013.01); *C12N 2501/599* (2013.01)

(58) Field of Classification Search
None
See application file for complete search history.

(56) References Cited

U.S. PATENT DOCUMENTS

| | | | |
|---|---|---|---|
| 7,378,276 B2 | 5/2008 | Ettinger et al. | |
| 7,438,907 B2 | 10/2008 | Schuuman et al. | |
| 7,534,772 B2 | 5/2009 | Weiner et al. | |
| 7,695,716 B2 | 4/2010 | Drachman et al. | |
| 8,815,543 B2 * | 8/2014 | Kitamura et al. | 435/70.1 |
| 9,206,247 B2 * | 12/2015 | Beaumont | C07K 14/4703 |
| 2004/0265315 A1 | 12/2004 | Dingivan | |
| 2009/0074711 A1 | 3/2009 | Glennie | |
| 2009/0123467 A1 | 5/2009 | Bedi et al. | |
| 2010/0266680 A1 | 10/2010 | Andre et al. | |
| 2011/0013566 A1 | 6/2011 | Tedder et al. | |
| 2011/0135666 A1 * | 6/2011 | Tedder | A61K 35/17 424/173.1 |
| 2012/0183535 A1 | 7/2012 | Buggy | |
| 2012/0214192 A1 | 8/2012 | Kitamura et al. | |
| 2013/0136754 A1 | 5/2013 | Tedder et al. | |
| 2013/0309211 A1 | 7/2013 | Tedder et al. | |
| 2016/0060598 A1 * | 3/2016 | Spits | C07K 16/00 435/326 |
| 2016/0244509 A1 * | 8/2016 | Spits | C07K 16/1027 |

FOREIGN PATENT DOCUMENTS

| | | | |
|---|---|---|---|
| WO | WO 98/50547 | 3/1999 | |
| WO | WO 01/10462 | 2/2001 | |
| WO | WO 04/053057 | 10/2004 | |
| WO | WO 2005000901 | 1/2005 | |
| WO | WO 2006/121852 | 11/2006 | |
| WO | WO 04/053452 | 8/2007 | |
| WO | WO 2008025848 | 3/2008 | |
| WO | 2009/047270 | 4/2009 | |
| WO | WO 2009/105150 | 8/2009 | |
| WO | 2009/131712 | 10/2009 | |
| WO | WO 2010132659 | 11/2010 | |
| WO | WO 2011/147903 | 12/2011 | |
| WO | 2012/019041 | 2/2012 | |
| WO | WO 2012/088272 | 6/2012 | |
| WO | WO2013076139 | * | 5/2013 |

OTHER PUBLICATIONS

Bouaziz et al. "Regulatory B cells as inhibitors of immune responses and inflammation," 2008 Immunol. Rev. 224:201-214.
Brummel, R. et al., "Activation of Marginal Zone B Cells from Lupus Mice with Type A(D) CpG-Oligodeoxynucleotides1," 2005 J. Immunol. 174:2429-34.
Brutkiewicz, R.R. et al., "TAP-independent, β2-Microglobulin-dependent surface expression of functional mouse CD1.1," 1995 J. Exp. Med. 182:1913-1919.
Cuss, A.K. et al., "Expansion of functionally immature transitional B cells is associated with human-immunodeficient states characterized by impaired humoral immunity," 2006 J. Immunol. 176:1506-1516).
DiLillo, D. J. et al., "B10 cells and regulatory B cells balance immune responses during inflammation, autoimmunity, and cancer," Ann. N. Y. Acad. Sci. 1183, 38-57 (2010).
Duan, B. et al., "Lupus resistance is associated with marginal zone abnormalities in an NZM murine model," 2007, Lab. Invest. 87:14-28.
Evans, J.G. et al., "Novel suppressive function of transitional 2 B Cells in experimental arthritis," 2007 J. Immunol. 178:7868-78.
Ferguson, T.A. et al., "Regulation of contact hypersensitivity by interleukin 10," (1994) J. Exp. Med. 179:1597-1604.
Fillatreau, S. et al., "B cells regulate autoimmunity by provision of IL-10," Nat. Immunol. 3, 944-950 (2002).
Gray, M. et al., "Apoptotic cells protect mice from autoimmune inflammation by the induction of regulatory B cells," 2007, Proc. Natl. Acad. Sci. USA 104:14080-5.
Haas, K. M. et al., "B-1a and B-1b cells exhibit distinct developmental requirements and have unique functional roles in innate and adaptive immunity to S. pneumoniae," 2005, Immunity 23:7-18.
Haas, K. M. et al., "Protective and pathogenic roles for B cells during systemic autoimmunity in NZB/W F1 mice," J. Immunol. 184, 4789-4800 (2010).

(Continued)

*Primary Examiner* — Michail Belyavskyi
(74) *Attorney, Agent, or Firm* — Andrus Intellectual Property Law, LLP

(57) ABSTRACT

Provided herein are methods of expanding B cells, and in particularly B10 cells capable of producing IL-10, ex vivo. The methods include incubation of harvested B cells in the presence of IL-21. Compositions comprising the ex vivo expanded B cells and methods of using the expanded B cell-containing compositions to treat diseases or conditions are also provided. Methods of assessing B10 cell function in a subject are also provided.

18 Claims, 7 Drawing Sheets

(56) References Cited

OTHER PUBLICATIONS

Hasegawa, M. et al., "B-lymphocyte depletion reduces skin fibrosis and autoimmunity in the tight-skin mouse model for systemic sclerosis," 2006, Am. J. Pathol. 169:954-66.
Harris, D.P. et al., "Reciprocal regulation of polarized cytokine production by effector B and T cells," 2000, Nat. Immunol. 1:475-82.
Hayakawa, I. et al., "B-lymphocyte depletion ameliorates Sjogren's syndrome in ld3 knockout mice," 2007, Immunology 122:73-9.
Huggins, J. et al., "CpG DNA activation and plasma-cell differentiation of CD27_ naïve human B cells," Blood 109(4):1611-1619 (2007).
Inoue, S. et al., "Inhibitory effects of B cells on antitumor immunity," 2006 Cancer Res. 66:7741-7747.
van Krieken, J.H.J.M. et al., "Splenic marginal zone lymphocytes and related cells in the lymph node: A morphologic and immunohistochemical study," 1989 Hum. Pathol. 20:320-325.
Kurosaki, T., "Paradox of B cell-targeted therapies," 2008 J. Clin. Inv. 118(10):3260-3263.
Lampropoulou, V. et al., "TLR-activated B cells suppress T cell-mediated autoimmunity," 2008 J. Immunol. 180:4763-4773.
Levesque, M.C. et al., "B cell-directed therapies for autoimmune disease and correlates of disease response and relapse," 2008 J. Allergy Clin. Immunol. 121:13-21.
Lund, et al., "Cytokine-producing B lymphocytes-key regulators of immunity," 2008 Curr. Op. Immunol. 20(3):332-338.
Makowska, A. et al., "CD1high B cells: A population of mixed origin," 1999 Eur. J. Immunol. 29:3285-3294.
Matsushita, et al., "Inhibitory role of CD19 in the progrssion of experimental autoimmune encephalomyelitis by regulating cytokine response," 2006 Am. J. Path., 168(3):812-821.
Matsushita, T. et al., "Regulatory B cells inhibit EAE initiation in mice while other B cells promote disease progression,". J. Clin. Invest. 118, 3420-3430 (2008).
Matsushita, et al., "B-lymphocyte depletion for the treatment of multiple sclerosis: Now things really get interesting," 2009 Expert Rev. Neurotherapeutics 9(3):309-312.
Mauri et al., "Prevention of arthritis by interleukin-10-producing B cells," 2003, J. Exp. Med. 197:489-501.
Minard-Colin, V. et al., "Lymphoma depletion during CD20 immunotherapy in mice is mediated by macrophage FcγRI, FcγRIII, and FcγRIV," 2008 Blood 112:1205-1213.
Mizoguchi, A. et al., "Chronic intestinal inflammatory condition generates IL-10-producing regulatory B cell subset characterized by CD1d upregulation," 2002 Immunity 16:219-30.
Mizoguchi, A. et al., "A case for regulatory B cells," 2006, J. Immunol. 176:705-710.
Sato, S. et al., "CD19 regulates B lymphocyte signaling thresholds critical for the development of B-1 lineage cells and autoimmunity," J. Immunol. 157, 4371-4378 (1996).
Schwarz, A. et al., "In vivo effects of interleukin-10 on contact hypersensitivity and delayed-type hypersensitivity reactions," 1994, J. Invest. Dermatol. 103:211-16.
Sims, G.P. et al., "Identification and characterization of circulating human transitional B cells," 2005 Blood 105:4390-4398.
Spencer, N.F. et al., "IL-12 directly stimulates expression of IL-10 by CD5+ B cells and IL-6 by both CD5+ and CD5- B cells: Possible involvement in age-associated cytokine dysregulation," 1997, Int. Immunol. 9:745-54.
Tian, J. et al. Lipopolysaccharide-activated B cells down-regulate Th1 immunity and prevent autoimmune diabetes in nonobese diabetic mice, 2001 J. Immunol. 167:1081-1089.
Uchida, J. et al, "The innate mononuclear phagocyte network depletes B lymphocytes through Fc receptor-dependent mechanisms during anti-CD20 antibody immunotherapy," 2004 J. Exp. Med. 199:1659-1669.
Yanaba, K. et al., "B cell depletion delays collagen-induced arthritis in mice: Arthritis induction requires synergy between humoral and cell-mediated immunity," 2007, J. Immunol. 179:1369-80.
Yanaba, K. et al., "A regulatory B cell subset with a unique CD1dhiCD5+ phenotype controls T cell-dependent inflammatory responses," Immunity 28, 639-650 (2008).
Yanaba, K. et al., "Regulatory B cells," 2009 Jap. Soc. Clin. Immunol. 32(3):135-141 (Abstract).
International Search Report and Written Opinion in International Patent Application No. PCT/US2009/002560 dated Jul. 20, 2010 (10 pages).
International Search Report and Written Opinion in International Patent Application No. PCT/US2011/046643 dated Mar. 14, 2012 (11 pages).
Bauer, S.R. et al., "Modulated Expression of the Epidermal Growth Factor-Like Homeotic Protein dlk Influences Stromal-Cell—Pre-B-Cell Interactions, Stromal Cell Adipogenesis, and Pre-B-Cell Interleukin-7 Requirements," Molecular and Cellular Biology 18(9):5247-5255 (1998).
Becker, P.D. et al., "Generation of human antigen-specific monoclonal IgM antibodies using vaccinated "human immune system" mice," PLoS One, 5(10):e13137 (2010).
Blair, P.A. et al., "CD19+CD24hiCD38h cells exhibit regulatory capacity in healthy individuals but are functionally impaired in systemic lupus erythematosus patients," 2010 Immunity 32:129-140.
Colliou, N. et al., "Long-Term Remissions of Severe Pemphigus After Rituximab Therapy Are Associated with Prolonged Failure of Desmoglein B Cell Response," Science Translational Medicine 5, 175ra30 (2013).
Fillatreau, S., "Novel regulatory functions for Toll-like receptor-activated B cells during intracellular bacterial infection," Immunol. Rev. 240, 52-71 (2011).
Huang, J. et al., "Isolation of human monoclonal antibodies from peripheral blood B cells," (2013) Nature Protocols 8(10):1907-1915.
Anolik, J.H. et al., "New treatments for SLE: Cell-depleting and anti-cytokine therapies," 2005 Best Practice & Research Clinical Rheumatology 19(5):859-878.
Asadullah, K. et al., "Interleukin-10 therapy—Review of a new approach," 2003 Pharmacol. Rev. 55:241-269.
Colgan, S.P. et al., "Ligation of intestinal epithelial CD1d induces bioactive IL-10: Critical role of the cytoplasmic tail in autocrine signaling," 1999 PNAS 96(24):13938-13943.
Dalwadi, H. et al., "B cell developmental requirement for the Gαi2 Gene1," 2003 J. Immunol. 170:1707-1715.
Hernandez, H.J. et al., "In infection with Schistosoma mansoni, B cells are required for T helper type 2 cell responses but not for granuloma formation," 1997 J. Immunology 158:4832-4837.
Horikawa, M. et al., "Regulatory B cell production of IL-10 inhibits lymphoma depletion during CD20 immunotherapy in mice," J. Clin. Invest. 121, 4268-4280 (2011).
Iwata, Y. et al., "Characterization of a rare IL-10-competent B cell subset in humans that parallels mouse regulatory B10 cells," Blood 117, 530-541 (2011).
Jiang, S. et al., "Regulatory T cells and transplantation tolerance," 2006 Human Immunol. 67:765-776.
Klein, U. et al., "Human immunoglobulin (1g)M+IgD+ peripheral blood B cells expressing the CD27 cell surface antigen carry somatically mutated variable region genes: CD27 as a general marker for somatically mutated (Memory) B Cells," 1998 J. Exp. Med. 188:1679-1689.
Kwakkenbos, M.J. et al., "Generation of stable monoclonal antibody-producing B cell receptor—positive human memory B cells by genetic programming," Nature Medicine 16(1):123-129.
Liu, R. et al., "A regulatory effect of IL-21 on T follicular helper-like cell and B cell in rheumatoid arthritis," Arthritis Research & Therapy 14(R255):1-12 (2012).
Lyons, J.-A. et al., "B cells are critical to induction of experimental allergic encephalomyelitis by protein but not by a short encephalitogenic peptide," 1999 Eur. J. Immunol. 29:3432-3439.
Mann, M. et al., "B cell regulation of CD4+CD25+ T regulatory cells and IL-10 via B7 is essential for recovery from experimental autoimmune encephalomyelitis1," 2007 J. Immunol. 178:3447-3456.

(56) References Cited

OTHER PUBLICATIONS

Maseda, D. et al., "Regulatory B10 cells differentiate into antibody-secreting cells after transient IL-10 production in vivo," J. Immunol. 188, 1036-1048 (2012).
Matsushita, T. et al., "Regulatory B cells (B10 cells) and regulatory T cells have independent roles in controlling EAE initiation and late-phase immunopathogenesis," J. Immunol. 185, 2240-2252 (2010).
Matsushita, T. et al., "Identifying regulatory B cells (B10 cells) that produce IL-10," Methods Mol. Biol. 677, 99-111 (2011).
Mauri, C. et al., "The 'short' history of regulatory B cells," 2008, Trends in Immunol. 29: 34-40.
Mauri C., "Regulation of immunity and autoimmunity by B cells," Curr. Opin. Immunol. 22, 761-767 (2010).
Nojima, T. et al., "In-vitro derived germinal centre B cells differentially generate memory B or plasma cells in vivo," Nature Comm. 2(465):1-11 (2011).
O'Garra, A. et al., "Ly1 B (B-1) cells are the main source of B cell-derived interleukin 10," 1992 Eur. J. Immunol. 22:711-717.
Ozaki, K. et al., "Regulation of B cell differentiation and plasma cell generation by IL-21, a novel inducer of Blimp-1 and Bcl-6," J. Immunol. 173, 5361-5371 (2004).
Paciorkowski, N. et al., "Primed Peritoneal B lymphocytes are sufficient to transfer protection against Brugia pahangi infection in mice," 2003 Infection and Immunity 71(3):1370-1378.
Pallier, A. et al., Patients with drug-free long-term graft function display increased numbers of peripheral B cells with a memory and inhibitory phenotype, Kidney International 78:503-513 (2010).
Poe, J. C. et al., "Amplified B lymphocyte CD40 signaling drives regulatory B10 cell expansion in mice," PLoS One 6, e22464 (2011).
Roncarolo, M.-G. et al., "Regulatory T-cell immunotherapy for tolerance to self antigens and alloangens in humans," 2007 Nature Reviews Immunol. 7:585-598.
Santos, M.A. et al., "Notch1 engagement by Delta-like-1 promotes differentiation of B lymphocytes to antibody-secreting cells," PNAS 104(39):15454-15459 (2007).
Sanz, I. et al., "Phenotypic and functional heterogeneity of human memory B cells," 2008 Sem. Immunol. 20:67-82.
Scheeren, F.A. et al., "Antigen-Specific Monoclonal Antibodies Isolated from B Cells Expressing Constitutively Active STAT5," PLoS One 6(4):e17189 (2011).
Sonoda, K.-H. et al., "CD1d on antigen-transporting APC and splenic marginal zone B cells promotes NKT cell-dependent tolerance," 2002 Eur. J. Immunol. 32:848-857.
Spolski, R. et al., "Interleukin-21: basic biology and implications for cancer and autoimmunity," Annu Rev Immunol 26, 57-79 (2008).
Spolski, R. et al., "IL-21 mediates suppressive effects via its induction of IL-10," J. Immunol. 182, 2859-2867 (2009).
Tangye, S.G. et al., "Identification of functional human splenic memory B cells by expression of CD148 and CD27," 1988 J. Exp. Med. 188:1691-1703.
Velupillai, P. et al., "B-1 cell (CD5+B220+) outgrowth in murine schistosomiasis is genetically restricted and is largely due to activation by polylactosamine sugars," 1997 J. of Immunology 158:338-344.
Watanabe, R. et al., "CD19 expression in B cells is important for suppression of contact hypersensitivity," 2007 American J. of Pathol. 171(2):560-570.
Wei, B. et al., "Mesenteric B cells centrally inhibit CD4+ T cell colitis through interaction with regulatory T cell subsets," 2005 PNAS 102(6):2010-2015.
Wolf, S.D. et al., "Experimental autoimmune encephalomyelitis induction in genetically B cell-deficient mice," 1996 J. Exp. Med. 184:2271-2278.
Xiu, Y. et al., "B lymphocyte depletion by CD20 monoclonal antibody prevents diabetes in nonobese diabetic mice despite isotype-specific differences in FcγR effector funcitons," 2008, J. Immunol. 180:2863-75.
Yanaba, K. et al., "The development and function of regulatory B cells expressing IL-10 (B10 cells) requires antigen receptor diversity and TLR signals," J. Immunol. 182, 7459-7472 (2009).
Yokoyama, S. et al., "Expression of the Blast-1 activation/adhesion molecule and its identification as CD48," 1991 J. Immunol. 146:2192-2200.
Zhang, X. et al., "Type I interferons protect neonates from acute inflammation through interleukin 10-producing B cells," 2007 J. of Experimental Medicine 204(5): 1107-1118.
Office Action for U.S. Appl. No. 12/989,468 dated Apr. 12, 2012 (7 pages).
Office Action for U.S. Appl. No. 12/989,468 dated Aug. 20, 2012 (9 pages).
Office Action for U.S. Appl. No. 12/989,468 dated Sep. 26, 2013 (9 pages).
International Search Report and Written Opinion in International Patent Application No. PCT/US2013/058484 dated Jan. 10, 2014 (10 pages).
International Preliminary Report on Patentability in International Patent Application No. PCT/US2013/058484 dated Mar. 19, 2015 (8 pages).
Armitage, R. J., Fanslow, W. C., Strockbine, L., Sato, T. A., Clifford, K. N., Macuduff, D. M., Anderson, D. M., Gimpel, S. D., Davis-Smith, T., Maliszewski, C. R., Clark, E. A., Smith, C. A., Grabstein, K. H., Cosman, D., and Spriggs, M. K., Molecular and biological characterization of a murine ligand for CD40. Nature, 1992, pp. 80-82, vol. 357.
Armitage, R. J., MacDuff, B. M., Spriggs, M. K., and Fanslow, W. C., Human B cell proliferation and Ig secretion induced by recombinant CD40 ligand are modulated by soluble cytokines. J. Immunol., 1993, pp. 3671-3680, vol. 150.
Borghesi, L. A., Smithson, G., and Kincade, P. W., Stromal cell modulation of negative regulatory signals that influence apoptosis and proliferation of B lineage lymphocytes. J Immunol, 1997, pp. 4171-4179, vol. 159.
Bossen, C., Ingold, K., Tardivel, A., Bodmer, J.L., Gaide, O., Hertig, S., Ambrose, C., Tschopp, J., and Schneider, P., Interactions of tumor necrosis factor (TNF) and TNF receptor family members in the mouse and human. J. Biol. Chem., 2006, pp. 13964-13971, vol. 281.
Cang, S., et al., Novel CD20 monoclonal antibodies for lymphoma therapy, Journal of Hematology and Oncology, 2012, 5:64.
Defrance, T., Vanbervliet, B., Briere, F., Durand, I., Rousset, F., and Banchereau, J., Interleukin 10 and transforming growth factor beta cooperate to induce anti-CD40-activated naive human B cells to secrete immunoglobulin A., J. Exp. Med., 1992, pp. 671-682, vol. 175.
Edgell, C.J., McDonald, C. C., and Graham, J. B., Permanent cell line expressing factor VIII-related antigen established by hybridization. Proc. Natl. Acad. Sci., 1983, pp. 3734-3737, vol. 80, USA.
El Zouhairi, M., et al., Molecularly targeted therapy for metastatic colon cancer: proven treatments and promising new agents, Gastrointest Cancer Res., 2011, 15-21, 4:1.
Ettinger, R. et al., IL-21 induces differentiation of human naive and memory B cells into antibody-secreting plasma cells. J. Immunol., 2005, pp. 7867-7879, vol. 175.
Ettinger, et al., IL-21 and BAFF/BLyS synergize in stimulating plasma cell differentiation from a unique population of human splenic memory B cells, J Immunol, 2007, pp. 2872-2882, vol. 178.
Federico, et al., Chronic inflammation and oxidative stress in human carcinogenesis, International Journal of Cancer, 2007; pp. 2381-2386, vol. 121.
Goodnow, C.C. et al., Altered immunoglobulin expression and functional silencing of self-reactive B lymphocytes in transgenic mice, Nature, 1988, pp. 676-682, vol. 334.
Haas, K. M. et al., CD22 ligand binding regulates normal and malignant B lymphocyte survival In Vivo, J. Immunol., 2006, pp. 3063-3073, vol. 177.
Husak, Z., Printz, D., Schumich, A., Potschger, U., and Dworzak, M. N., Death induction by CD99 ligation in TEL/AML1-positive acute lymphoblastic leukemia and normal B cell precursors. J. Leukocyte Biol., 2010, pp. 405-412, vol. 88.

(56) References Cited

OTHER PUBLICATIONS

Jabara, H. H., Fu, S. M., Geha, R. S., and Vercelli, D., CD40 and IgE: synergism between anti-CD40 monoclonal antibody and interleukin-6 in the induction of IgE synthesis by highly purified human B cells. J. Exp. Med., 1990, pp. 1861-1864, vol. 17:6.
Jin, H., Carrio, R., Yu, A., and Malek, T. R., Distinct activation signals determine whether IL-21 induces B cell costimulation, growth arrest, or Bim-dependent apoptosis. J Immunol, 2004, pp. 657-665, vol. 173.
Kincade, P. W., Lee, G., Pietrangeli, C. E., Hayashi, S. I., and Gimble, J. M., Cells and molecules that regulate B lymphopoiesis in bone marrow. Annu. Rev. Immunol., 1989, pp. 111-143, vol. 7.
Kincade, P. W., Molecular interactions between stromal cells and B lymphocyte precursors. Semin Immunol, 1991, pp. 379-390, vol. 3.
Kincade, P. W., Cell interaction molecules and cytokines which participate in B lymphopoiesis. Baillieres Clin Haematol, 1992, pp. 575-598, vol. 5.
Lebien, T. W., and Tedder, T. F., B-lymphocytes: How they develop and function. Blood, 2008, pp. 1570-1579, vol. 112.
Lesley, J., He, Q., Miyake, K., Hamann, A., Hyman, R., and Kincade, P. W., Requirements for hyaluronic acid binding by CD44: a role for the cytoplasmic domain and activation by antibody. J. Exp. Med., 1992, pp. 257-266, vol. 175.
Li, X., Steeber, D. A., Tang, M.L.K., Farrar, M. A., Perlmutter, R. M., and Tedder, T. F., Regulation of L-selectin-mediated rolling through receptor dimerization. J. Exp. Med., 1998 188:1385-1390.
Maini, R.N., et. al., How does infliximab work in rheumatoid arthritis, Arthritis Res., 2002, 4 Supp 2:S22-8.
Martin, F. et al., Marginal zone and B1 B cells unite in the early response against T-independent blood-borne particulate antigens, Immunity, 2001, pp. 617-629, vol. 14.
Mauri, C. et al., Therapeutic activity of agonsitic monoclonal antibodies against CD40 in a chronic autoimmune inflammatory process, Nat Med, 2000, pp. 673-679, vol. 6.
Mehta, D. S. et al., IL-21 induces the apoptosis of resting and activated primary B cells. J Immunol, 2003, pp. 4111-4118, vol. 170.
Miyake, K., Underhill, C. B., Lesley, J., and Kincade, P. W., Hyaluronate can function as a cell adhesion molecule and CD44 participates in hyaluronate recognition. J. Exp. Med., 1990, pp. 69-75. vol. 172.
Miyake, K., Medina, K., Ishihara, K., Kimoto, M., Auerbach, R., and Kincade, P. W, A VCAM-like adhesion molecule on murine bone marrow stromal cells mediates binding of lymphocyte precursors in culture. J Cell Biol, 1991, pp. 557-565, vol. 114.
Miyake, K., Medina, K. L., Hayahi, S.I., Ono, S., Hamaoka, T., and Kincade, P. W., Monoclonal antibodies to Pgp-1/CD44 block lymphohematopoiesis in long term bone marrow cultures. J. Exp. Med., 1990, pp. 477-488, vol. 171.
Nadiri, A., Poylak, M. J., Jundi, M., Alturaihi, H., Reyes-Moreno, C., Hassan, G. S., and Mourad, W., CD40 translocation to lipid rafts: Signaling requirements and downstream biological events. Eur. J. Immunol, 2011, pp. 2358-2367, vol. 41.
Neron, S., Racine, C., Roy, A., and Guerin, M., Differential responses of human B-lymphocytes subpopulations to gradedl levels of CD40-CD154 interaction. Immunology, 2005, pp. 454-463, vol. 116.

Nummela, P., Lammi, J., Soikkeli, J., Saksela, O., Laakkonen, P., and Holtta, E., Transforming growth factor beta-induced (TGFBI) is an anti-adhesive protein regulating the invasive growth of melanoma cells. The American journal of pathology, 2012, pp. 1663-1674, vol. 180.
Ozaki, K., et al. A critical role for IL-21 in regulating immunoglobulin production, Science, 2002, pp. 1630-1634, vol. 298.
Poe, et al., CD22 regulates B lymphocyte function in vivo through both ligand-dependent and ligand-independent mecahnaisms, Nat Immunol, 2004, pp. 1078-1087, vol. 5.
Rousset, F., Garcia, E., and Banchereau, J., Cytokine-induced proliferation and immunoglobulin production of human B lyphocytes triggered through their CD40 antigen. J. Exp. Med., 1991, pp. 705-710, vol. 173.
Rousset, F., Garcia, E., Defrance, T., Peronne, C., Vezzio, N., Hsu, D.H., Kastelein, R., Moore, K.W., and Banchereau, J., Interleukin 10 is a potent growth and differentiation factor for activated human B lymphocytes. Proc. Natl. Acad. Sci., 1992, pp. 1890-1893, vol. 89, USA.
Scheeren, F. A., Van Lent, A. U., Nagasawa, M., Weijer, K., Spits, H., Legrand, N., and Blom, B., Thymic stromal lymphopoietin induces early human B-cell proliferation and differentiation. Eur. J. Immunol., 2010, pp. 955-965, vol. 40.
Thomas, M., Calamito, M., Srivastava, B., Maillard, I., Pear, W.S., and Allman, D., Notch activity synergizes with B-cell-receptor and CD40 signaling to enhance B-cell activation. Blood, 2007, pp. 3342-3350, vol. 109.
Wang, H., Beaty, N., Chen, S., Qi, C.F., Masiuk, M., Shin, D. M., and Morse, H. C. 3rd., The CXCR7 chemokine receptor promotes B-cell retention in the splenic marginal zone and serves as a sink for CXCL12. Blood, 2012, pp. 465-468, vol. 119.
Wehr, C., et al., A new CD21low B cell population in the peripheral blood of patients with SLE, Clin. Immunol., 2004, pp. 161-171, vol. 113.2.
Weitzman, S.A. and Gordon, L.I, et al., Inflammation and cancer: role of phagocyte-generated oxidants in carcinogenesis, Blood, 1990, pp. 655-663, vol. 76.
Yasui, T., Muraoka, M., Takaoka-Shichijo, Y., Ishida, I., Takegahara, N., Uchida, J., Kumanogoh, A., Suematsu, S., Suzuki, M., and Kikutani, H., Dissection of B cell differentiation during primary immune responses in mice with altered CD40 signals, Intl. Immunol., 2002, pp. 319-329, vol. 14.
Yoshizaki, A., et al., Regulatory B cells control T cell autoimmunity through IL-21-dependent cognate interactions, Nature, 2012, pp. 264-268, vol. 491.
Zhang, K., Clark, E. A., and Saxon, A., CD40 stimulation provides an IFN-γ-independent and IL-4-dependent differentiation directly to human B cells for IgE production., J. Immunol., 1991, pp. 1836-1842, vol. 146.
Zhou, L.J. et al., Tissue-specific expression of the human CD19 gene in transgenic mice inhibits antigen-independent B lymphocyte development, Mol. Cell. Biol., 1994, pp. 3884-3894, vol. 14.
Konforte, Danijela, et al., IL-21: An Executor of B Cell Fate, J Immunology, 2009, pp. 1781-1787, vol. 182.
Tortola, Luigi, et al., IL-21 induces death of marginal zone B cells during chronic inflammation, Blood, 2010, pp. 5200-5207, vol. 116, No. 24.

* cited by examiner

METHODS OF EXPANDING AND ASSESSING B CELLS AND USING EXPANDED B CELLS TO TREAT DISEASE

CROSS-REFERENCE TO RELATED APPLICATIONS

This patent application claims the benefit of priority of U.S. Provisional Patent Application No. 61/697,663, filed Sep. 6, 2012 and U.S. Provisional Patent Application No. 61/707,256, filed Sep. 28, 2012, both of which are incorporated herein by reference in their entireties.

STATEMENT REGARDING FEDERALLY SPONSORED RESEARCH

This invention was made with United States government support awarded by the National Institutes of Health grant number A1057157 and U19 A156363. The United States may have certain rights in this invention.

INTRODUCTION

It is well-known that B cells regulate immune responses by producing antigen-specific antibody. However, specific B cell subsets can also negatively regulate immune responses, validating the existence of regulatory B cells. Human and mouse regulatory B cells (B10 cells) with the ability to express the inhibitory cytokine interleukin-10 (IL-10) have been identified. Although rare, B10 cells are potent negative regulators of antigen-specific inflammation and T cell-dependent autoimmune disease in mice. B10 cell IL-10 production regulates antigen-specific immune responses in vivo without inducing systemic immunosuppression. B10 cells may thereby be useful in regulating or controlling inflammation or autoimmune diseases.

SUMMARY

Provided herein are methods of expanding B cells ex vivo, compositions comprising expanded B cells and methods of using the expanded B cell compositions for assessing or screening for a disease state or condition and for treating diseases as described herein. Methods of expanding B10 cells capable of producing IL-10 ex vivo by culturing or incubating B cells harvested and isolated from a subject with IL-21 are provided herein. The resultant expanded polyclonal B cells can be collected or isolated from the culture and may be further harvested to select for B10 cells.

The methods of expanding B cells ex vivo include culturing B cells harvested from a subject on feeder cells expressing a CD40 agonist and a B cell survival promoter such as BAFF in the presence of IL-4 and then culturing the resultant cells on feeder cells expressing a C40 agonist and a B cell survival promoter such as BAFF in the presence of IL-21 prior to collecting or isolating the expanded polyclonal B cells. The expanded polyclonal B cells may also be further selected. For example, the expanded polyclonal B cells may be further selected to isolate B10 cells.

Compositions comprising the expanded polyclonal B cells and B10 cells produced by the methods described herein are also provided. The composition comprising the expanded polyclonal B cells produced by the methods described herein may be further selected to produce a composition comprising B10 cells. The compositions of expanded polyclonal B cells and/or B10 cells may be used in a variety of methods to treat various diseases or conditions. Pharmaceutical compositions including the expanded polyclonal B cell and B10 cell compositions described herein are also provided.

Methods of treating a subject having an autoimmune disease, an allergic disorder, an inflammatory disorder or immunodeficiency are provided. The methods include administering a therapeutically effective amount of the compositions comprising expanded polyclonal B cells or B10 cells described herein to a subject in need of treatment for an autoimmune disease, an allergic disorder, an inflammatory disorder or an immunodeficiency.

Methods of treating a subject to prevent or treat organ, tissue or cell transplant rejection or associated graft versus host disease are also provided. The methods include administering a therapeutically effective amount of the compositions including the B cells and/or B10 cells described herein to a subject in need of treatment for transplant rejection or graft versus host disease.

Methods of treating a subject receiving recombinant, therapeutic or xenogeneic protein(s) are also provided. The methods include administering a therapeutically effective amount of the compositions including the B cells and/or B10 cells disclosed herein to a subject in need of treatment for a genetic, transplantation, allergy, inflammation, or autoimmune disorder.

Methods of assessing B10 cell function in a subject are also provided. In these methods, the B cells are harvested from a sample from the subject and cultured in the presence of IL-21 for at least 24 hours. The B cells are then tested to determine whether the cells are capable of producing IL-10 and/or the amount of IL-10 produced or the percentage of cells capable of producing IL-10 in the culture as compared to a control having normal B cell function is determined. B cells expressing IL-10 are B10 cells. The B cells may be cultured on feeder cells expressing a CD40 agonist and a B cell survival promoter such as BAFF in the presence of IL-4 and subsequently in the presence of IL-21 prior to assessment of the ability of the cells to produce IL-10.

The methods of assessing B10 cell function provided herein may be used to diagnose an autoimmune or inflammatory disease or may be used to assess the stage of a disease or condition in the subject.

BRIEF DESCRIPTION OF THE DRAWINGS

FIG. 1A is a set of FACS analysis dot plots and graphs of the data showing that IL-21 induces B10 cell IL-10 production and secretion. Spleen CD19$^+$ B cells purified from wild type mice were cultured in medium alone or with the indicated recombinant cytokines or LPS. To visualize IL-10-competent B cells, LPS, PMA, ionomycin and monensin (L+PIM) were added to the cultures 5 h before the cells were isolated, stained with CD19 mAb, permeabilized, stained for cytoplasmic IL-10 expression and analyzed by flow cytometry. Representative histograms show IL-10$^+$ cell frequencies within the indicated gates, with background staining shown for cells cultured with monensin (Mon.) alone. Bar graphs indicate mean (±SEM) IL-10$^+$ B cell frequencies or culture supernatant fluid IL-10 concentrations at 48 or 72 h from three independent experiments using individual mice. FIG. 1B is a set of dot plots showing that IL-21 induces CD1d$^{hi}$CD5$^+$ B cell IL-10 production. Purified spleen CD1d$^{hi}$CD5$^+$ or CD1d$^{lo}$CD5$^-$ B cells from wild type mice were cultured with media alone or containing IL-21 for 48 h before IL-10$^+$ B cell frequencies were assessed as in (FIG. 1A). FIG. 1C is set of graphs showing that B10 cells express IL-21R. CD19$^+$ splenocytes purified from wild type mice were cultured with L+PIM for 5 h before cell surface CD19 and IL-21R, and cytoplasmic IL-10 staining to identify IL-10-competent B10 cells (dot plot, left panel). Representative IL-21R expression by IL-10$^+$ and IL-10$^-$ B cells from wild type mice is shown in comparison with control B cells from IL-21R$^{-/-}$ mice (gray histograms). These results are representative of three independent experiments using individual mice. FIG. 1) is a set of graphs showing that IL-21R expression is required for B10 cell expansion in vivo following MOG immunization. B10 cell numbers were assessed in wild type, IL-21R$^{-/-}$ or C19$^{-/-}$ mice 7 days after receiving PBS or MOG$_{35-55}$ immunization. Representative flow cytometry histograms are shown. Bar graphs indicate mean (±SEM) B10 cell frequencies (≥3 mice per group). FIG. 1A and FIG. 1D, Significant differences between sample means are indicated; *, $p<0.05$; **, $p<0.01$.

FIG. 2A shows the experimental protocol and resulting disease severity in various mice after administration of MOG$_{35-55}$. One day before CD19$^{-/-}$ or wild type (WT) mice were immunized with MOG$_{35-55}$ on day 0, the CD$^{-/-}$ mice received saline (PBS) or purified spleen CD1d$^{hi}$CD5$^+$ or CD1d$^{lo}$CD5$^-$ B cells from either wild type, IL-10$^{-/-}$, IL-21R$^{-/-}$, CD40$^{-/-}$, or MHC-II$^{-/-}$ mice. The mice were scored daily thereafter for disease severity. The top two graphs show data from the same experiment, but were separated since the curves superimposed and thus were difficult to visualize on a single graph. FIG. 2B is a set of graphs showing that B10 cells require MHC-II expression to regulate EAE severity in wild type mice treated with CD20 or control mAb 7 days before MOG$_{35-55}$ immunization on day 0. The mice also received PBS or purified CD1d$^{hi}$CD5$^+$ B cells from either CD20$^{-/-}$ or MHC-II$^{-/-}$ CD20$^{-/-}$ mice 1 day before MOG$_{35-55}$ immunization. The two graphs are from the same experiment, but were separated to facilitate visualization of the overlapping curves. FIG. 2C is a graph showing that activated MHC-II$^{-/-}$ B10 cells are not able to reduce disease severity in wild type mice. Purified CD1d$^{hi}$CD5$^+$ B cells from wild type or MHC-II$^{-/-}$ mice were cultured with agonistic CD40 mAb for 48 h to induce B10pro cell maturation, with LPS added during the final 5 h of culture. Wild type mice were given either PBS or CD1d$^{hi}$CD5$^+$ B cells 1 day before MOG$_{35-55}$ immunization on day 0. In FIGS. 2A-2C values represent mean (±SEM) symptom scores from ≥3 mice in each group, with similar results obtained in three independent experiments. Significant differences between sample means are indicated; *, $p<0.05$.

FIG. 3A is a set of dot plots and graphs showing that B10 cells require IL-10, IL-21R, CD40 and MHC-II expression to regulate antigen-specific T cell proliferation in vivo. CD19$^{-/-}$ recipient mice were given PBS as a control, or purified CD1d$^{hi}$CD5$^+$ or CD1d$^{lo}$CD5$^-$ B cells from naïve wild type (WT), IL-10$^{-/-}$, IL-21R$^{-/-}$, CD40$^{-/-}$ or MHC-II$^{-/-}$ mice, or wild type mice with EAE (day 28) 1 day before MOG$_{35-55}$ immunization on day 0. Four days after immunization, dye (CFSE)-labeled TCR$^{MOG}$ CD4$^+$Thy1.1$^+$ T cells were transferred into CD19$^{-/-}$ recipient mice. Five days later, peripheral lymph node CD4$^+$Thy1.1$^+$ T cells were analyzed for proliferation, with representative flow cytometry analysis of CFSE dilution shown. Bar graphs indicate mean (±SEM) numbers of divided TCR$^{MOG}$ T cells. FIG. 3B is a set of dot plots and graphs showing that B10 cells require IL-10, IL-21R, CD40 and MHC-II expression for their regulation of antigen-specific T cell cytokine production. Purified CD1d$^{hi}$CD5$^+$ B cells from the indicated mice were transferred into CD19$^{-/-}$ recipient mice 1 day before MOG$_{35-55}$ immunization on day 0, with TCR$^{MOG}$ Thy1.1$^+$CD4$^+$ T cells transferred on day 4. Fourteen days later, lymph node Thy1.1$^+$CD4$^+$ T cells were analyzed for IL-17 and IFN-γ production by intracellular cytokine staining, with representative flow cytometry results shown. Bar graphs indicate mean (±SEM) frequencies of cytokine-expressing cells, with three mice in each group. In FIGS. 3A and 3B, significant differences between sample means are indicated: *, $p<0.05$; **, $p<0.01$. FIG. 3C shows a model for autoantigen (Ag)-specific B10 cell function. B cells capture autoantigens that trigger appropriate BCR signals (step 1) and promote IL-10-competent B10pro cell development. During immune responses (step 2), B10pro cells present peptides to antigen-specific T cells through cognate interactions that induce T cell activation and CD40/CD154 interactions. Activated T cells may produce IL-21 locally, which binds to proximal B10 cell IL-21R (step 3). IL-21R signals induce B10 cell IL-10 production and effector function (B10eff, step 4), which may negatively regulate antigen-specific T cell function (step 5).

FIG. 4A is a set of dot plots showing B10 cell development in vitro. Purified spleen B cells were cultured on a monolayer of NIH-3T3 cells expressing CD154/BLyS in the presence of exogenous IL-4 for 4 days, then cultured on fresh NIH-3T3-CD154/BLyS cells with exogenous IL-21 for 3 or 5 days as indicated. The cells were then isolated, cultured with monensin for 5 h and stained for cytoplasmic IL-10 expression. Representative IL-10$^+$ B cell frequencies within the indicated gates are shown. Similar results were obtained in ≥10 experiments. FIG. 4B is a superimposed bar and line graph showing that IL-21 drives B10 cell expansion in vitro. B cells were cultured as in FIG. 4A with cells harvested each day of culture. Bar values represent mean (±SEM) B cell and B10 cell numbers, or B10 cell frequencies (solid line) from three independent experiments. FIG. 4C is a set of dot plots showing IL-21-induced 10 cells to express CD5. Wild type B cells were cultured for 9 days as in FIG. 4A and stained for CD5 and CD19 expression. CD5$^+$ and CD5$^-$ B cells were then purified by cell sorting and cultured with monensin for 5 h before cytoplasmic IL-10 staining. Results shown are representative of three independent experiments. FIG. 4D is a set of graphs showing that IL-21-induced B10 effector cells inhibit EAE initiation and progression. IL-21-induced B10 cells (CD5$^+$CD19$^+$) or non-B10 cells (CD5$^-$CD19$^+$) were isolated as in FIG. 4C and adoptively transferred into wild type mice on days −1, 7, 14 or 21 (arrows) before/after MOG immunization and EAE induction as in FIG. 2. FIG. 4E is a bar graph showing that B10 cell expansion in vitro requires IL-21R and CD40 expression, and in vivo BCR signaling. Purified spleen B cells isolated from wild type, IL-21R$^{-/-}$, CD40$^{-/-}$, MHC-II$^{-/-}$, CD19$^{-/-}$, or MD4 mice were cultured as in FIG. 4A, with mean (±SEM) cell numbers quantified after culture. Values represent means (±SEM) of three independent experiments. IL-10$^+$ B cell frequencies in the cultures are shown in parentheses. FIG. 4F is a set of graphs showing that IL-21-induced B10 cells require IL-10 and MHC-II expression to inhibit EAE. B cells from IL-10$^{-/-}$ or MHC-II$^{-/-}$ mice were cultured as in FIG. 4A, separated into CD5$^+$ or CD5$^-$ cells as in FIG. 4C and adoptively transferred into wild type mice before MOG$_{35-55}$ immunization as in FIG. 4D. In FIGS. 4D and 4F, values represent mean (±SEM) symptom scores from ≥3 mice in each group, with similar results obtained in three independent experiments. In FIGS. 4B, 4D and 4E, significant differences between sample means are indicated: *, p<0.05; **, p<0.01.

FIG. 5A is a set of bar graphs showing that IL-21 induces B10 cell IL-10 production and secretion. Spleen $CD19^+$ B cells purified from wild type mice were cultured with medium alone or with the indicated cytokines for 48 or 72 h. To visualize IL-10-competent cells, monensin was added to the cultures 5 h before the cells were isolated, stained with CD19 mAb, permeabilized, stained for cytoplasmic IL-10 expression and analyzed by flow cytometry. Bar graphs indicate mean (±SEM) $IL-10^+$ B cell frequencies or numbers at 48 and 72 h from individual mice in three independent experiments. Significant differences between media versus cytokine sample means are indicated: *, p<0.05; **, p<0.01. FIG. 5B-D are a set of dot plots and bar graphs showing IL-21R. CD40 and MHC-II expression are not required for B10 or B10pro cell development, respectively. Purified spleen B cells from wild type and $IL-21R^{-/-}$ (FIG. 5B) $CD40^{-/-}$ (FIG. 5C) or $MHC-II^{-/-}$ (FIG. 5D) mice were cultured with monensin alone or L+PIM for 5 h to quantify B10 cell frequencies. Alternatively, B10-B10pro cell frequencies were determined after culturing the cells ex vivo with agonistic CD40 mAb for 48 h, with L+PIM added during the final 5 h of culture. Representative histograms and bar graphs indicate mean (±SEM; ≥3 mice per group) percentages and numbers of B cells that expressed IL-10 in one of two experiments with equivalent results.

DETAILED DESCRIPTION

Figure 1:
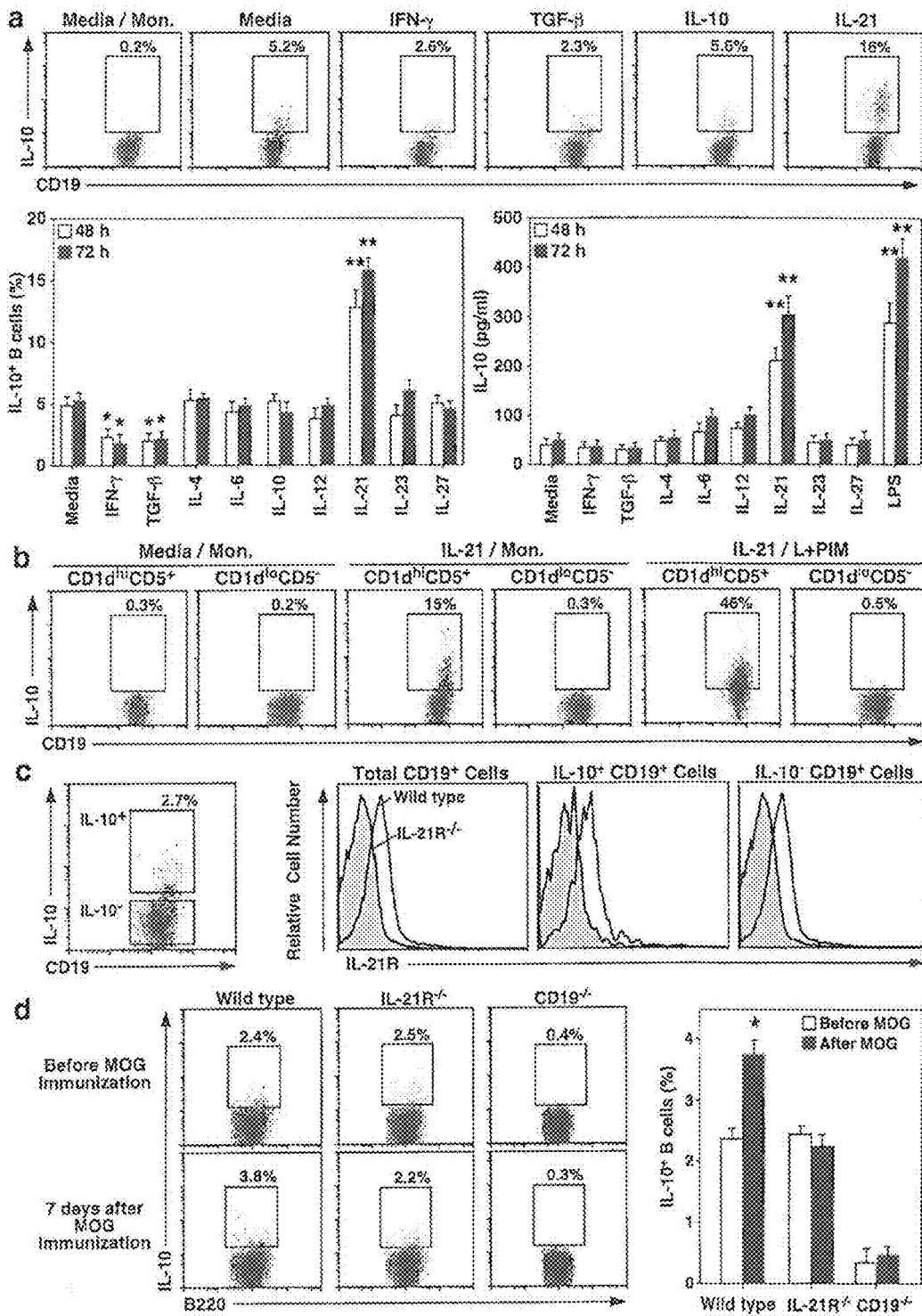
FIG. 1 is a set of data which demonstrate that IL-21 induces regulatory B10 cell function.

The B10 cell subset of regulatory B cells has been functionally defined in humans and mice by their ability to express IL-10. B cells that are competent to express IL-10 following 5 h of ex vivo phorbol ester and ionomycin stimulation are functionally defined as B10 cells to distinguish them from other regulatory B cells that modulate immune responses through other mechanisms. B10 cells are found at low frequencies (1-5%) in naïve mice but expand with autoimmunity. Spleen B10 cells are predominantly found within the minor $CD1d^{hi}CD5^+$ B cell subpopulation along with rare B10 progenitor (B10pro) cells that are induced to become IL-10-competent during in vitro culture with agonistic CD40 monoclonal antibody (mAb). The capacity of human and mouse B10 cells to produce IL-10 is central to their ability to negatively regulate inflammation and autoimmune disease, as well as adaptive and innate immune responses, but the physiologic signals that control IL-10 production in vivo are unknown.

B10 cell immunoregulation is antigen-specific, and B cell antigen receptor (BCR) specificity dramatically influences B10 cell development. Receptors or pathways that positively or negatively regulate BCR signaling can also modulate B10 cell numbers in vivo. For example, CD19-deficient ($CD19^{-/-}$) mice are essentially devoid of regulatory B10 cells, which leads to exacerbated inflammation and disease symptoms during contact hypersensitivity and in the experimental autoimmune encephalomyelitis (EAE) model of multiple sclerosis. IL-10 itself is not required for B10 cell development since B cells with the capacity to express IL-10 reporter genes develop normally in $IL-10^{-/-}$ mice. B10 cell numbers are also normal in T cell-deficient nude mice and in mice deficient in expression of major histocompatibility complex class II (MHC-II) or CD40 molecules that are important for cognate B cell-T cell interactions. Consequently, appropriate BCR signals are thought to select a subset of B cells to become IL-10-competent B10 cells. Innate pathogen-induced signals also influence regulatory B10 cell development in vivo. Little is otherwise known about how B10 cell IL-10 production is regulated in vivo, and it remains unclear how such rare B cells exert such potent in vivo effects and selectively inhibit antigen-specific T cell function during inflammation and autoimmunity.

Using a mouse model for multiple sclerosis, we show here that B10 cell maturation into functional IL-10-secreting effector cells that inhibit in vivo autoimmune disease requires IL-21 and CD40-dependent cognate interactions with T cells. Moreover, the ex vivo provision of CD40 and IL-21 receptor signals can drive B10 cell development and expansion by up to four-million-fold and generate B10 effector cells producing IL-10 that dramatically inhibit disease symptoms when transferred into mice with established autoimmune disease. Thereby, the ex vivo expansion and reinfusion of autologous 10 cells may provide a novel and effective in vivo treatment for autoimmune diseases and other conditions that are resistant to current therapies.

In addition, we also show that human B cells and B10 cells can be expanded ex vivo. The B cells were harvested from normal human blood and expanded ex vivo using the same methods as were used for expansion of mouse B cells. As described in the Examples, B cell numbers were increased by 130 fold while B10 cells were increased by 5-6,000 fold. Thus, the examples demonstrate that the methods may be used to generate ex vivo expanded B cells that may be useful for autologous treatment of human diseases or conditions in which addition of responsive B cells or of B10 cells may be therapeutic.

Methods of Expanding B Cells Ex Vivo

Described herein are methods of expanding polyclonal B cells and specifically B10 cells ex vivo. The methods include harvesting B cells from a subject and incubating them with IL-21. In FIG. 1, the B10 cells were expanded over two fold after 48 hours of ex vivo incubation with IL-21 at 100 ng/ml and over three fold after 72 hours incubation. The methods may further include incubation with a CD40 ligand, and a B cell survival promoter such as BAFF (BLyS, used interchangeably herein) or feeder cells expressing a CD40 ligand and/or BAFF to result in further expansion of B cells and B10 cells. As shown in the Examples, the B cells may be further expanded ex vivo by a first incubation with IL-4 followed by a second incubation including IL-21. Either or both of these steps may include feeder cells and optionally a CD40 ligand and/or BAFF. Total B cells were expanded using the methods described herein, but B10 cells were expanded at a higher frequency using these methods. In addition, the B10 cells were able to produce IL-10 without a need for further stimulation ex vivo with LPS or another stimulatory signal. Suitably, the B cells are human B cells.

In an alternative embodiment of the methods of expanding B cells described herein, the B cells are harvested from a subject and then incubated on feeder cells expressing a CD40 agonist and a B cell survival promoter such as BAFF in the presence of IL-4. This incubation period may last from two to ten or more days and the amount of IL-4 may be optimized. In the methods, 2 ng/ml IL-4 was used, but 0.5 ng/ml to 100 ng/ml may be useful. The resultant cells were then incubated on the feeder cells expressing CD40 agonist and a B cell survival promoter such as BAFF in the presence of IL-21 for an additional two to eight or more days before harvesting the expanded B cells. In the Examples, either 10 ng/ml or 100 ng/ml of IL-21 was used, but between 5 ng/ml and 1000 ng/ml of IL-21 may be used. The actual amount of IL-4 and IL-21 used in the methods can be determined by those of skill in the art and will depend on the culture conditions, including whether the culture media and the cytokines were replenished over time, the length of the culture period and other culture conditions. In the Examples, total polyclonal B cells and B10 cells were expanded using this method. However, the cultures may start with single B cells or isolated B cell subsets that are then expanded ex vivo into monoclonal, pauciclonal or polyclonal B cell populations. The B cells produce antibodies under the culture conditions described herein and thus the methods may be used to select for a monoclonal, pauciclonal or polyclonal population of antibody producing B cells. Suitably, the B cells are mouse B cells, Suitably the B cells are human B cells.

The B cells used in the methods may be harvested from various areas of the subject, including but not limited to the blood, spleen, peritoneal cavity, lymph nodes, bone marrow, site of autoimmune disease, site of inflammation or tissue undergoing transplant rejection in the subject. The cells may be harvested from the subject by any means available to those of skill in the art. The harvested population of cells should contain B cells, but may be a mixed cellular population. The subject may be any animal with B lymphocytes, suitably a mammal, suitably a domesticated animal such as a horse, cow, pig, cat, dog, or chicken, or suitably a human. Alternatively, the cells may be derived from stem cells, including but not limited to B cell stem cells, bone marrow stem cells, embryonic stem cells and induced pluripotent stem cells, which have been appropriately differentiated in vitro to develop into B cells or B cell progenitors prior to use in the methods described herein. See e.g., Carpenter et al. 2011, Blood 117: 4008-4011.

The B cells may be isolated from the subject by removal of non-B cells, or selection for cell surface markers such as IgM, IgD, IgG, IgA, IgE, CD19, CD20, CD21, CD22, CD24, CD40, CD72. CD79a or CD79b, or combinations of these cell surface molecules including CD1d, CD5, CD9, CD10, CD23, CD27, CD38, CD48, CD80, CD86, CD138 or CD148. The expanded B cells may be harvested by selecting for these markers after ex vivo culturing in the method or specific B cell types, such as B10 cells, may be selected using these markers before or after ex vivo expansion either alone or in combination. The B10 cells may be harvested by selecting for CD1d, CD5, CD24, CD27 or combinations thereof. In some embodiments, the B10 cells are capable of producing IL-10 after incubation with IL-21 and thus may be selected, isolated or harvested by selecting for IL-10 production. In other embodiments, the B10 cells may need to be further stimulated to produce IL-10 with e.g. LPS or PMA and ionomycin. Methods of stimulating B10 cells to produce IL-10 are known in the art and include stimulation with LPS or CpG oligonucleotides.

As used herein expansion of B cells includes stimulation of proliferation of the cells as well as prevention of apoptosis or other death of the cells. As used herein, "culturing" and "incubation" are used to indicate that the cells are maintained in cell culture medium at 37° C. and 5% $CO_2$ for a period of time with the indicated additives (feeder cells, cytokines, agonists, other stimulatory molecules or media, which may include buffers, salts, sugars, serum or various other constituents). Suitably, the incubation or culturing periods used herein is at least 48 hours, but may be for any amount of time up to eight or more days. As shown in the Examples more than one culturing period may be used. In the Examples, for mouse B cell expansion the culture with IL-4 was four days long and the culture with IL-21 was five days. For human B cells, the expansion with IL-4 was a seven day culture period followed by a five day culture with IL-21. Those of skill in the art will appreciate that the culturing or incubation time may be varied to allow proper expansion, to adjust for different cell densities or frequencies of individual subsets, and to allow an investigator to properly time use of the cells. Thus the precise culture length may be determined empirically by one of skill in the art.

As used herein, isolating is used to indicate that a group of cells is separated from incubation media, feeder cells or other non-B cells. Isolating is not meant to convey that the resulting isolated cells have a certain level of purity or homogeneity. The cells may be harvested, isolated or selected using any means available to those of skill in the art. For example, B cells may be harvested from adherent cells by selecting for non-adherent cells after an appropriate incubation. Cells may also be selected for expression of cell surface markers by FACS sorting or by the differential ability to bind antibody coated magnetic beads. Means of selecting cells in a mixed population are well known to those skilled in the art.

Non-limiting examples of CD40 agonists include CD40 antibodies and fragments thereof, the CD40 ligand (CD154) and polypeptide fragments thereof, small molecules, synthetic drugs, peptides (including cyclic peptides), polypeptides, proteins, nucleic acids, aptamers, synthetic or natural inorganic molecules, mimetic agents, and synthetic or natural organic molecules. In a certain embodiment, the CD40 agonist is a CD40 antibody. The CD40 antibodies can be of any form. Antibodies to CD40 are known in the art (see, e.g., Buhtoiarov et al., 2005, J. Immunol. 174:6013-22; Francisco et al., 2000, Cancer Res. 60:3225-31; Schwulst et al., 2006, 177:557-65, herein incorporated by reference in their entireties). The CD40 agonists may be CD40 ligands and may be expressed on the surface of feeder cells or soluble.

The BAFF (BLyS) may be expressed by the feeder cells via methods known to those of skill in the art. The BLyS may be expressed on the surface or may be soluble after cleaved from the cell surface. Alternatively the BAFF is replaced by a different factor(s) that promotes B cell survival in culture including feeder cells, BAFF fragments, APRIL, CD22 ligand, CD22 monoclonal antibody, or fragments thereof.

The feeder cells used in the Examples were fibroblasts but other feeder cells may be used in the methods. The feeder cells may be endothelial cells, epithelial cells, keratinocytes, melanocytes, or other mesenchymal or stromal cells. The incubation or culturing periods used in the methods may be from two to ten or more days for each step in the method. Suitably, the incubation time is between three and seven days, suitably it is between four and five days. As described in the examples the feeder cells are likely required to supply additional signals, other than the CD40 agonist and BAFF, to allow optimal B cell expansion in the methods. A preliminary analysis of other factors supplied by the feeder cells to optimize B cell expansion is included in the Examples and Table 1 below. In summary, in addition to a CD40 agonist and BAFF, the feeder cells minimally express VCAM-1 and CD44 in addition to CD40 agonist and BAFF. Increased expression of CD24, interleukin-7 (IL-7), Mst1 and Tslp by the feeder cells correlated with the feeder cells being capable of producing increased numbers of B cells during ex vivo expansion. Similarly, downregulation of certain molecules in the feeder cells correlated with increased ability to support B cell expansion. In particular, downregulation of CD99, TGFBI, CXCR7, Dlk1, Jag1 and Notch1 on the feeder cells correlated with the cells being better capable of supporting B cell expansion ex vivo. Thus, those of skill in the art may be able to select for, or create via genetic engineering, feeder cells better capable of supporting B cell expansion ex vivo. The information may also be used to generate a means of expanding B cells that does not require live feeder cells for optimal ex vivo B cell expansion.

The methods may allow from two fold to over $5\times10^6$ fold expansion of B cells or B10 cells in particular. The cells may be selected after the culture period to remove any non-B cells or to positively select for B cells or for a particular B cell subset such as B10 cells. The B10 cells may represent 10%, 15%, 20%, 25%, 30%, 35%, 40% or more of the total B cells in the culture after the expansion method is complete. After selecting the cells for cell surface expression of a B10 cell surface marker(s) more than 50%, 55%, 60%, 65%, 70%, 75%, 80%, 85%, 90%, 95% of the cells are B10 or B10pro cells capable of producing IL-10.

Compositions Comprising the Expanded B Cells

Compositions including the expanded polyclonal B cells generated using the methods described herein are also provided. In one aspect, the compositions include more than 50%, 55%, 60%, 65%, 70%, 75%, 80%, 85%, 90%, 95%, 98%, 99% or substantially 100% B10 or B10pro cells. In other aspects the compositions are selected to include antibody producing B cells. The compositions may include more than 50%, 55%, 60%, 65%, 70%, 75%, 80%, 85%, 90%, 95%, 98%, 99% or substantially 100% antibody producing B cells.

The expanded B cell containing compositions may be used to make pharmaceutical compositions. Pharmaceutical compositions comprising the expanded B cells described above and a pharmaceutically acceptable carrier are provided. A pharmaceutically acceptable carrier is any carrier suitable for in vivo administration of cells. Examples of pharmaceutically acceptable carriers suitable for use in the composition include, but are not limited to, buffered solutions, glucose solutions, oil-based or cellular culture based fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer).

The expanded B cell compositions may be co-administered with other treatments, such as small molecule, polypeptide, antibody, aptamer or other therapeutics. Co-administration of the compositions described herein with another therapeutic may be administered in any order, at the same time or as part of a unitary composition. The two compositions may be administered such that one composition is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

In another embodiment, the B cell or B10 cell population may be monoclonal or pauciclonally expanded from isolated single cells or isolated B cell subsets. In one aspect, the compositions include more than 10%, 15%, 20%, 25%, 30%, 35%, 40%, 45%, 50%, 55%, 60%, 65%, 70%, 75%, 80%, 85%, 90%, 95%, 98%, 99% or substantially 100% monoclonal B cells or B10 cells. In other aspects the compositions are selected to include antibody producing B cells. The compositions may include more than 10%, 15%, 20%, 25%, 30%, 35%, 40%, 45%, 50%, 55%, 60%, 65%, 70%, 75%, 80%, 85%, 90%, 95%, 98%, 99% or substantially 100% antibody producing B cells. In another aspect the compositions are selected to include monoclonal or pauciclonal antigen-specific B cells. The compositions may include more than 10%, 15%, 20%, 25%, 30%, 35%, 40%, 45%, 50%, 55%, 60%, 65%, 70%, 75%, 80%, 85%, 90%, 95%, 98%, 99% or substantially 100% B cells specific for or producing antibody against a single protein or other antigenic entity. In another aspect, the compositions may include more than 50%, 55%, 60%, 65%, 70%, 75%, 80%, 85%, 90%, 95%, 98%, 99% or substantially 100% B cells capable of exerting regulatory activities by expressing IL-10. IL-2. IL-4. IL-5. IL-6, IL-12. IL-13, IL-17, IFNγ, IL-23 or TNF-α.

In another embodiment, the B cell or B10 cell population can be made responsive to a certain antigen involved in a specific disease. The B cells may produce therapeutic antibodies or other cytokines in response to subsequent encounter with the antigen. The B10 cell population, when sensitized with a certain antigen, may produce therapeutic amounts of IL-10 upon subsequent encounters with the antigen. Such antigen-specific B cell or B10 cell populations may be used in adoptive transfer methods, wherein a subject is or has previously been immunized with a certain antigen and the antigen-sensitized cells from said subject are isolated, expanded ex vivo by the methods described herein and transplanted to the same or another subject. Alternatively, a B cell or B10 cell population from a subject can be isolated and subsequently can be sensitized with a disease-specific antigen ex vivo or in vitro. The sensitized cell population can then be transplanted into the original or another subject by any method known in the art. In still another embodiment, the antigen-specific B cell or B10 cell population can be added to an implantable immune modulation device. According to this embodiment, the implanted cell population will produce strategically localized IL-10, antibody or another cytokine production when encountering antigen in the host, depending on the cells implanted. In a further aspect, the B cell or B10 cell population and a disease-specific antigen can both be placed in an implantable immune modulation device, and said device then can be transplanted into a recipient at a location where the therapeutic effects of the cell population, i.e., IL-10 production, antibody production or cytokine production, are needed, thus resulting in an amplified response to the disease in vivo.

In another aspect, a certain disease-specific antigen can be administered in conjunction with a CD40 agonist or a TLR agonist. The therapeutic agent may be an antibody, in particular, a CD40 antibody or LPS or CpG oligodeoxynucleotides. In other aspects, the therapeutic agent is a small molecule, a polypeptide, DNA, or RNA that interacts with the B cell CD40 receptor or TLRs.

Any antigen from any disease, disorder, or condition may be used in accordance with the methods of the invention. Exemplary antigens include but are not limited to bacterial, viral, parasitic, allergens, autoantigens and tumor-associated antigens. If a DNA based vaccine is used the antigen will typically be encoded by a sequence of the administered DNA construct. Alternatively, if the antigen is administered as a conjugate the antigen will typically be a protein comprised in the administered conjugate. Particularly, the antigen can include protein antigens, peptides, whole inactivated organisms, and the like.

Specific examples of antigens that can be used include, but are not limited to, antigens from hepatitis A, B, C or D, influenza virus, *Listeria. Clostridium botulinum*, tuberculosis, tularemia, *Variola major* (smallpox), viral hemorrhagic fevers, *Yersinia pestis* (plague), HIV, herpes, pappilloma virus, and other antigens associated with infectious agents. Other antigens include antigens associated with autoimmune conditions, inflammatory conditions, allergy, asthma and transplant rejection. Non-limiting examples of autoimmune diseases and inflammatory diseases are provided, infra. As noted above, a B10 cell population sensitized with a disease-specific antigen can be administered alone or in conjunction with other therapeutic agents, such as a CD40 agonist or TLR in particular, a CD40 antibody, for use as a therapeutic or prophylactic vaccine for treating a disease condition or for suppressing immunity. Similarly, an expanded B cell composition sensitized with a disease or microbe specific antigen may confer immunity against such disease conditions or microbes.

In another embodiment, a B10 cell subset may be sensitized with antigen from a prospective transplant donor, so as to increase the levels of IL-10 production by the B10 cells in a transplant recipient. The increased IL-10 production by the B10 cell subset in the transplant recipient results in a decreased immune/inflammatory response to the transplant in the transplant recipient. The role of B10 cells in transplants is described more fully below.

Methods of Using the Expanded B Cell Compositions

The expanded B cell compositions may be used in methods of treating subjects having a disease or condition. Such adoptive transfer of B cells, and in particular B10 cells, can be effective to suppress a wide variety of diseases, including, but not limited to autoimmune diseases, inflammatory diseases, or any other disease which may be treated by introduction of a B cell or B10 cell population into a subject. Adoptive transfer of B cells or B10 cells can further be employed to minimize the immune/inflammatory response associated with transplant of cells and/or tissues.

In an exemplary adoptive transfer protocol, a mixed population of cells is initially extracted from a target donor. Suitably, the B cells are selected, more suitably the B10 and B10pro cells are selected from the subject. The cells isolated from the donor may be isolated from any location in the donor in which they reside including, but not limited to, the blood, spleen, lymph nodes, and/or bone marrow of the donor as described more fully above. Depending on the application, the cells may be extracted from a healthy donor; a donor suffering from a disease that is in a period of remission or during active disease; or from the organs, blood, or tissues of a donor that has died. In the case of the latter, the donor is an organ donor. In yet another embodiment, the cells can be obtained from the subject, expanded and/or activated and returned to the subject.

Harvested lymphocytes may be separated by flow cytometry or other cell separation techniques based on B cell markers or B10 cell specific cell markers such as those described previously (e.g., CD1d, CD5, CD24, and CD27), and then transfused to a recipient. See also International Application Nos. PCT/US2009/002560, PCT/US2011/46643 and PCT/US2011/066487, each of which is incorporated herein by reference in its entirety. Alternatively, the cells may be stored for future use. In one aspect of this embodiment, the donor and the recipient are the same subject. In another aspect of this embodiment, the donor is a subject other than the recipient. In a further aspect of this embodiment, the "donor" comprises multiple donors other than the recipient, wherein the B10 cells from said multiple donors are pooled. As discussed above, the B cells obtained from the donor are expanded using the methods provided herein. The cells may also be enriched, or made to produce elevated levels of IL-10 by methods available to those of skill in the art prior to being administered to a recipient.

In the methods of using the expanded B cells contemplated herein, wherein the donor is a subject other than the recipient, the recipient and the donor are histocompatible. Histocompatibility is the property of having the same, or mostly the same, alleles of a set of genes called the major histocompatibility complex (MHC). These genes are expressed in most tissues as antigens. When transplanted cells and/or tissues are rejected by a recipient, the bulk of the immune system response is initiated through the MHC proteins. MHC proteins are involved in the presentation of foreign antigens to T cells, and receptors on the surface of the T cell are uniquely suited to recognition of proteins of this type. MHC are highly variable between individuals, and therefore the T cells from the host may recognize the foreign MHC with a very high frequency leading to powerful immune responses that cause rejection of transplanted tissue. When the recipient and the donor are histocompatible, the chance of rejection of the B10 cell population by the recipient is minimized.

The amount of B cells or B10 cells which will be effective in the treatment and/or suppression of a disease or disorder which may be treated by introduction of a B cell or B10 cell population into a subject can be determined by standard clinical techniques. The dosage will depend on the type of disease to be treated, the severity and course of the disease, the composition being administered, the purpose of introducing the B cell or B10 cell population, previous therapy the recipient has undertaken, the recipient's clinical history and current condition, and the discretion of the attending physician. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions of the invention, such as by means of an appropriate conventional pharmacological or prophylactic protocol. The number of cells administered in the composition may also be determined empirically.

The B10 cell population can be administered in treatment regimes consistent with the disease, e.g., a single or a few doses over one to several days to ameliorate a disease state or periodic doses over an extended time to inhibit disease progression and prevent disease recurrence. For example, the composition may be administered two or more times separated by 4 hours, 6 hours, 8 hours, 12 hours, a day, two days, three days, four days, one week, two weeks, or by three or more weeks. The precise dose to be employed in the formulation will also depend on the route of administration, the seriousness of the disease or disorder, and whether the disease is chronic in nature and should be decided according to the judgment of the practitioner and each patient's circumstances.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce symptoms of the condition at least 10% P, 20%, 30%, 40%, 50%, 60%, 70%, 80%, 90% or 100% compared to pre-treatment symptoms or symptoms is left untreated. It is specifically contemplated that pharmaceutical preparations and compositions may palliate or alleviate symptoms of the disease without providing a cure, or, in some embodiments, may be used to cure the disease or disorder. Effective doses may be extrapolated from dose-response curves derived from in vitro or animal model test systems. Exemplary, non-limiting doses that could be used in the treatment of human subjects range from at least $4 \times 10^4$, at least $4 \times 10^5$, at least $4 \times 10^6$, at least $4 \times 10^7$, at least $4 \times 10^8$, at least $4 \times 10^9$, or at least $4 \times 10^{10}$ B cells/m². In a certain embodiment, the dose used in the treatment of human subjects ranges from about $4 \times 10^8$ to about $4 \times 10^{10}$ B cells/m².

For use in the methods described herein, the compositions may be administered by any means known to those skilled in the art, including, but not limited to, intraperitoneal, parenteral, intravenous, intramuscular, subcutaneous, or intrathecal. Thus the compositions may suitably be formulated as an injectable formulation. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

In another aspect, the B cells or B10 cells obtained from the donor can be introduced into a recipient at a desired location, so as to specifically target the therapeutic effects of the B cell or B10 cell population, i.e., IL-10 production or antibody secretion. Such techniques can be accomplished using implantable immune modulation devices, e.g., virtual lymph nodes, such as those described in U.S. patent application publication No. 2003/0118630; WO1999/044583; and U.S. Pat. No. 6,645,500, which are incorporated by reference herein in their entireties. According to this embodiment, a B cell or B10 cell population can be isolated from a donor as described above, added to an implantable immune modulation device, and said device then can be implanted into a recipient at a location where the therapeutic effects of the B cell or B10 cell population, i.e., antibodies or IL-10 production, are needed.

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is an inhibition or delay in the progression of the condition and/or prevention or delay of the onset of a disease or illness. The terms "treat," "treating" or "treatment of" also means managing an autoimmune disease or disorder. Thus, the terms "treat," "treating" or "treatment of" (or grammatically equivalent terms) refer to both prophylactic and therapeutic treatment regimes.

As used herein, a "sufficient amount" or "an amount sufficient to" achieve a particular result refers to a number of B10 or B10 effector cells of the invention that is effective to produce a desired effect, which is optionally a therapeutic effect (i.e., by administration of a therapeutically effective amount). For example, a "sufficient amount" or "an amount sufficient to" can be an amount that is effective to alter the severity of the subject's condition.

A "therapeutically effective" amount as used herein is an amount that provides some improvement or benefit to the subject. Alternatively stated, a "therapeutically effective" amount is an amount that provides some alleviation, mitigation and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject. It is likely that the "therapeutically effective" number of cells required to "treat" an individual will depend on the source of the B cells, the immunological status of the patient at time of blood harvest, the condition of the individual at the time of treatment, and the level of therapeutic treatment with immunosuppressive drugs or agents at the time of treatment as well-known to those skilled in the art.

Specific Diseases or Conditions Treatable in the Methods
Autoimmune Diseases

Diseases and conditions associated with diminished IL-10 levels can be treated in accordance with this aspect of the invention. Decreased levels of IL-10 have been demonstrated in autoimmune and inflammatory diseases including, but not limited to psoriasis (Asadullah et al., 1998, J. Clin. Investig. 101:783-94, Nickoloff et al., 1994, Clin. Immunol. Immunopathol., 73:63-8, Mussi et al. 1994, J. Biol. Regul. Homeostatic Agents), rheumatoid arthritis (Jenkins et al., 1994, Lymphokine Cytokine Res. 13:47-54; Cush et al., 1995, Arthritis Rheum. 38:96-104; Al Janadi et al., 1996, J. Clin. Immunol. 16:198-207), allergic contact dermatitis (Kondo et al., 1994, J. Investig. Dermatol. 103:811-14; Schwarz et al., 1994, J. Investig. Dermatol. 103:211-16), inflammatory bowel disease (Kuhn et al., 1993, Cell 75:263-74; Lindsay and Hodgson, 2001, Aliment. Pharmacol. Ther. 15:1709-16) and multiple sclerosis (Barrat et al., 2002, J. Exp. Med. 195:603-16; Cua et al., 2001, J. Immunol. 166: 602-8; Massey et al., 2002, Vet. Immunol. Immunopathol. 87:357-72; Link and Xiao, 2001. Immunol. Rev. 184:117-28).

Any type of autoimmune disease can be treated in accordance with this method of the invention. The term "autoimmune disease or disorder" refers to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

Exemplary autoimmune diseases or disorders include, but are not limited to: allergic contact dermatitis, allergic reactions to drugs, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid and associated skin diseases, cardiomyopathy, Celiac disease, Celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, cutaneous necrotizing venulitis, discoid lupus, erythema multiforme, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic/autoimmune thrombocytopenia purpura (ITP), immunologic lung disease, immunologic renal disease, IgA neuropathy, juvenile arthritis, lichen planus, lupus erthematosus, Méniere's disease, mixed connective tissue disease, multiple sclerosis, type 1 or immune-mediated diabetes mellitus, myasthenia gravis, pemphigus-related disorders (e.g., pemphigus vulgaris), pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, rheumatic fever, sarcoidosis, scleroderma, Sjögren's syndrome, stiff-man syndrome, spondyloarthropathies, systemic lupus erythematosis (SLE), lupus erythematosus, systemic vasculitis, takayasu arteritis, temporal arteristis/giant cell arteritis, thrombocytopenia, thyroiditis, ulcerative colitis, uveitis, vasculitides such as dermatitis herpetiformis vasculitis, vitiligo, and Wegener's granulomatosis.

The diagnosis of an autoimmune disease or disorder is complicated in that each type of autoimmune disease or disorder manifests differently among patients. This heterogeneity of symptoms means that multiple factors are typically used to arrive at a clinical diagnosis. Generally, clinicians use factors, such as, but not limited to, the presence of autoantibodies, elevated cytokine levels, specific organ dysfunction, skin rashes, joint swelling, pain, bone remodeling, and/or loss of movement as primary indicators of an autoimmune disease or disorder. For certain autoimmune diseases or disorders, such as RA and SLE, standards for diagnosis are known in the art. For certain autoimmune diseases or disorders, stages of disease have been characterized and are well known in the art. These art recognized methods for diagnosing autoimmune diseases and disorders as well as stages of disease and scales of activity and/or severity of disease that are well known in the art can be used to identify patients and patient populations in need of treatment for an autoimmune disease or disorder using the compositions and methods described herein.

Diagnostic criteria for different autoimmune diseases or disorders are known in the art. Historically, diagnosis is typically based on a combination of physical symptoms. More recently, molecular techniques such as gene-expression profiling have been applied to develop molecular definitions of autoimmune diseases or disorders. Exemplary methods for clinical diagnosis of particular autoimmune diseases or disorders are provided below. Other suitable methods will be apparent to those skilled in the art. Also provided are methods of diagnosing and/or staging an autoimmune disease based on B10 cell numbers or activity in a subject.

In certain embodiments of the invention, patients with low levels of autoimmune disease activity or patients with an early stage of an autoimmune disease (for diseases where stages are recognized) can be identified for treatment using the B10 cell compositions and methods provided herein. The early diagnosis of autoimmune diseases is difficult due to the general symptoms and overlap of symptoms among diseases. In such embodiments, a patient treated at an early stage or with low levels of an autoimmune disease activity has symptoms comprising at least one symptom of an autoimmune disease or disorder. In related embodiments, a patient treated at an early stage or with low levels of an autoimmune disease has symptoms comprising at least 1, 2, 3, 4, 5, 6, 7, 8, 9, 10, 11, 12, 13, 14, or 15 symptoms of an autoimmune disease or disorder. The symptoms may be of any autoimmune diseases and disorders or a combination thereof. Examples of autoimmune disease and disorder symptoms are described below.

Rheumatoid Arthritis

Rheumatoid arthritis is a chronic disease, mainly characterized by inflammation of the lining, or synovium, of the joints. It can lead to long-term joint damage, resulting in chronic pain, loss of function and disability. Identifying patients or patient populations in need of treatment for rheumatoid arthritis is a process. There is no definitive test that provides a positive or negative diagnosis of rheumatoid arthritis. Clinicians rely on a number of tools including, medical histories, physical exams, lab tests, and X-rays.

Physical symptoms vary widely among patients and commonly include, but are not limited to, joint swelling, joint tenderness, loss of motion in joints, joint malalignment, fatigue, stiffness (particularly in the morning and when sitting for long periods of time), weakness, flu-like symptoms (including a low-grade fever), pain associated with prolonged sitting, the occurrence of flares of disease activity followed by remission or disease inactivity, rheumatoid nodules or lumps of tissue under the skin (typically found on the elbows, they can indicate more severe disease activity), muscle pain, loss of appetite, depression, weight loss, anemia, cold and/or sweaty hands and feet, and involvement of the glands around the eyes and mouth, causing decreased production of tears and saliva (Sjögren's syndrome). Apart from physical symptoms, clinicians commonly use tests, such as, but not limited to, complete blood count, erythrocyte sedimentation rate (ESR or sed rate). C-reactive protein, rheumatoid factor, antinuclear antibodies (ANA), imaging studies, radiographs (X-rays), magnetic resonance imaging (MRI) of joints or organs, joint ultrasound, and bone densitometry (DEXA). These tests are examples of tests that can be used in conjunction with the compositions and methods described herein to check for abnormalities that might exist (i.e., identify patients or patient populations in need of treatment) or to monitor side effects of drugs and check progress.

Early symptoms of rheumatoid arthritis commonly are found in the smaller joints of the fingers, hands and wrists. Joint involvement is usually symmetrical, meaning that if a joint hurts on the left hand, the same joint will hurt on the right hand. In general, more joint erosion indicates more severe disease activity.

Symptoms of more advanced disease activity include damage to cartilage, tendons, ligaments and bone, which causes deformity and instability in the joints. The damage can lead to limited range of motion, resulting in daily tasks (grasping a fork, combing hair, buttoning a shirt) becoming more difficult. Skin ulcers, greater susceptibility to infection, and a general decline in health are also indicators of more advanced disease activity.

Progression of rheumatoid arthritis is commonly divided into three stages. The first stage is the swelling of the synovial lining, causing pain, warmth, stiffness, redness and swelling around the joint. Second is the rapid division and growth of cells, or pannus, which causes the synovium to thicken. In the third stage, the inflamed cells release enzymes that may digest bone and cartilage, often causing the involved joint to lose its shape and alignment, more pain, and loss of movement.

Molecular techniques can also be used to identify patients or patient populations in need of treatment. For example, rheumatoid arthritis has been shown to be associated with allelic polymorphisms of the human leukocyte antigen (HLA)-DR4 and HLA-DRB1 genes. Rheumatoid arthritis patients frequently express two disease-associated HLA-DRB1*04 alleles. Patients can be tested for allelic polymorphisms using methods standard in the art. MHC genes are not the only germline-encoded genes influencing susceptibility to RA that can be used to diagnose or identify patients or patient populations in need of treatment. Female sex clearly increases the risk, and female patients develop a different phenotype of the disease than do male patients. Any molecular indicators of rheumatoid arthritis can be used to identify patients or patient populations in need of treatment with B10 cell compositions and methods described herein.

In certain embodiments of the methods, a patient can be treated with B10 cell compositions prior, concurrent, or subsequent to other therapies, such as, but not limited to surgery. For example, patients in need of treatment for rheumatoid arthritis commonly undergo surgical treatment, such as, but not limited to synovectomy to reduce the amount of inflammatory tissue by removing the diseased synovium or lining of the joint; arthroscopic surgery to take tissue samples, remove loose cartilage, repair tears, smooth a rough surface or remove diseased synovial tissue; osteotomy, meaning "to cut bone," this procedure is used to increase stability by redistributing the weight on the joint; joint replacement surgery or arthroplasty for the surgical reconstruction or replacement of a joint; or arthrodesis or fusion to fuse two bones together. Such surgical procedures are examples of treatment that patients can undergo prior, concurrent, or subsequent to treatment with the methods and compositions provided herein. In one embodiment, the B10 cell compositions may be administered locally at the site of surgery either before, during or after surgery to protect the joint from further attack or degradation.

Systemic Lupus Erythematosis (SLE)

Systemic lupus erythematosis (SLE) is a chronic (long-lasting) rheumatic disease which affects joints, muscles and other parts of the body. Patients or patient populations in need of treatment for SLE can be identified by examining physical symptoms and/or laboratory test results. Physical symptoms vary widely among patients. For example, in SLE, typically 4 of the following 11 symptoms exist before a patient is diagnosed with SLE: 1) malar rash: rash over the checks; 2) discoid rash: red raised patches; 3) photosensitivity: reaction to sunlight, resulting in the development of or increase in skin rash; 4) oral ulcers: ulcers in the nose or mouth, usually painless; 5) arthritis: nonerosive arthritis involving two or more peripheral joints (arthritis in which the bones around the joints do not become destroyed); 6) serositis pleuritis or pericarditis: (inflammation of the lining of the lung or heart); 7) renal disorder, excessive protein in the urine (greater than 0.5 gm/day or 3+ on test sticks) and/or cellular casts (abnormal elements the urine, derived from red and/or white cells and/or kidney tubule cells); 8) neurologic disorder: seizures (convulsions) and/or psychosis in the absence of drugs or metabolic disturbances which are known to cause such effects; 9) hematologic disorder: hemolytic anemia or leukopenia (white blood count below 4,000 cells per cubic millimeter) or lymphopenia (less than 1,500 lymphocytes per cubic millimeter) or thrombocytopenia (less than 100,000 platelets per cubic millimeter) (The leukopenia and lymphopenia must be detected on two or more occasions. The thrombocytopenia must be detected in the absence of drugs known to induce it); 10) antinuclear antibody: positive test for antinuclear antibodies (ana) in the absence of drugs known to induce it; and/or 11) immunologic disorder: positive anti-double stranded anti-DNA test, positive anti-sm test, positive antiphospholipid antibody such as anticardiolipin, or false positive syphilis test (vdrl).

Other physical symptoms that may be indicative of SLE include, but are not limited to, anemia, fatigue, fever, skin rash, muscle aches, nausea, vomiting and diarrhea, swollen glands, lack of appetite, sensitivity to cold (Raynaud's phenomenon), and weight loss.

Laboratory tests can also be used to identify patients or patient populations in need of treatment. For example, a blood test can be used to detect a group of autoantibodies found in the blood of almost all people with SLE; a compliment test (C3, C4, CH50, CH100) can be used to measure the amount of complementary proteins circulating in the blood, a sedimentation rate (ESR) or C-reactive protein (CRP) may be used to measure inflammation levels, a urine analysis can be used to detect kidney problems, chest X-rays may be taken to detect lung damage, and an EKG can be used to detect heart problems. These tests are examples of tests that can be used in conjunction with the compositions and methods described herein to check for abnormalities that might exist (i.e., identify patients or patient populations in need of treatment) or to monitor side effects of drugs and check progress.

Idiopathic/Autoimmune Thrombocytopenia Purpura (ITP)

Idiopathic/autoimmune thrombocytopenia purpura (ITP) is a disorder of the blood characterized by immunoglobulin G (IgG) autoantibodies that interact with platelet cells resulting in destruction of those platelet cells. Typically, the antibodies are specific to platelet membrane glycoproteins. The disorder may be acute (temporary, lasting less than 2 months) or chronic (persisting for longer than 6 months). Patients or patient populations in need of treatment for ITP can be identified by examining a patient's medical history, physical symptoms, and/or laboratory test results.

Physical symptoms include purplish-looking areas of the skin and mucous membranes (such as the lining of the mouth) where bleeding has occurred as a result of a decrease in the number of platelet cells. The main symptom is bleeding, which can include bruising ("ecchymosis") and tiny red dots on the skin or mucous membranes ("petechiae"). In some instances bleeding from the nose, gums, digestive or urinary tracts may also occur. Rarely, bleeding within the brain occurs. Common signs, symptoms, and precipitating factors also include, but are not limited to, abrupt onset (childhood ITP), gradual onset (adult ITP), nonpalpable petechiae, purpura, menorrhagia, epistaxis, gingival bleeding, hemorrhagic bullae on mucous membranes, signs of GI bleeding, menometrorrhagia, evidence of intracranial hemorrhage, nonpalpable spleen, retinal hemorrhages, recent live virus immunization (childhood ITP), recent viral illness (childhood ITP), spontaneous bleeding when platelet count is less than 20,000/mm$^3$, and bruising tendency.

Laboratory tests that can be used to diagnose ITP include, but are not limited to, a complete blood count test, or a bone marrow examination to verify that there are adequate platelet-forming cells (megakaryocyte) in the marrow and to rule out other diseases such as metastatic cancer and leukemia. Isolated thrombocytopenia is the key finding regarding laboratory evaluation. Giant platelets on peripheral smear are indicative of congenital thrombocytopenia. A CT scan of the head may be warranted if concern exists regarding intracranial hemorrhage. These tests are examples of tests that can be used in conjunction with the compositions and methods described herein to check for abnormalities that might exist (i.e., identify patients or patient populations in need of treatment) or to monitor side effects of drugs and check progress.

Pemphigus-Related Disorders

Pemphigus-related disorders are characterized by a blistering condition of the skin caused by the attack of antibodies of certain proteins on the surface of skin cells. This attack interferes with the ability of the skin cells to bind to each other. There are three main types of pemphigus: pemphigus vulgaris, pemphigus foliaceus and paraneoplastic pemphigus. Patients or patient populations in need of treatment for pemphigus-related disorders can be identified by examining a patient's medical history, physical symptoms, and/or laboratory test results.

Typically, diagnosis of these pemphigus-related disorders is made by skin biopsy. The biopsy skin sample can be treated using a direct immunofluorescence technique to detect desmoglein antibodies in the skin. Another diagnostic test that may be used is called indirect immunofluorescence or antibody titer test. This measures desmoglein autoantibodies in the blood serum. It may be used to obtain a more complete understanding of the course of the disease. In addition, a serum assay for desmoglein antibodies, an ELISA, is also available. It is the most accurate. The presence of these desmoglein autoantibodies in biopsy samples is diagnostic of pemphigus generally.

Pemphigus vulgaris can be diagnosed by the presence of blisters in the mouth. Inflammation or erosions may also be present in the lining of the eye and eyelids, and the membranes of the nose or genital tract. Half of the patients also develop blisters or erosions of the skin, often in the groin, underarm, face, scalp and chest areas. Pemphigus foliaceus is a superficial, relatively mild form of pemphigus. It usually manifests on the face and scalp, but also involves the back and chest. Lesions do not occur in the mouth. The blisters are more confined to the outermost surface and often itch. Paraneoplastic pemphigus is very rare and generally occurs in people who have cancer. The lesions are painful and affect the mouth, lips and esophagus (swallowing tube) as well as the skin. Due to involvement of the airways, signs of respiratory disease may occur and can be life-threatening. These tests are examples of tests that can be used in conjunction with the compositions and methods described herein to check for abnormalities that might exist (i.e., identify patients or patient populations in need of treatment) or to monitor side effects of drugs and check progress.

Autoimmune Diabetes

A patient in need of treatment for type 1 diabetes can be treated with the B10 cell compositions and methods described herein as well. Type 1 diabetes is an autoimmune disease, in which the body's immune system damages the islet cells in the pancreas, reducing the production of insulin, resulting in high blood sugar. Patients or patient populations in need of treatment for autoimmune diabetes can be identified by examining a patient's medical history, physical symptoms, and/or laboratory test results. Symptoms often come on suddenly and include, but are not limited to, increased thirst, increased urination, constant hunger, weight loss, blurred vision, and fatigue.

Laboratory tests that can be used in identifying patients or patient populations in need of treatment for autoimmune diabetes include, but are not limited to, the direct measurement of glucose levels in the blood during an overnight fast, and measurement of the body's ability to appropriately handle the excess sugar presented after drinking a high glucose drink. For the first test, an elevated blood sugar level after an overnight fast (not eating anything after midnight) can be used as a diagnostic factor. A value above 140 mg/dl on at least two occasions typically means a patient has diabetes. Normal patients have fasting sugar levels that generally run between 70-110 mg/dl. For the second test, an oral glucose tolerance test is typically performed. The patient being tested starts the test in a fasting state (having no food or drink except water for at least 10 hours but not greater than 16 hours). An initial blood sugar is drawn and then the patient is given a "glucola" bottle with a high amount of sugar in it (75 grams of glucose), (or 100 grams for pregnant women). The patient then has their blood tested again 30 minutes, 1 hour, 2 hours and 3 hours after drinking the high glucose drink. These tests are examples of tests that can be used in conjunction with the compositions and methods described herein to check for abnormalities that might exist (i.e., identify patients or patient populations in need of treatment) or to monitor side effects of drugs and check progress.

Scleroderma

Scleroderma is a chronic skin and connective tissue disease. In general, it is characterized by the formation of scar tissue in the skin and organs of the body. Identification of patients and patient populations in need of treatment of scleroderma can be based on clinical history and physical findings. Patients or patient populations in need of treatment for sclerodermna can be identified by examining a patient's medical history, physical symptoms, and/or laboratory test results. Diagnosis may be delayed in patients without significant skin thickening. Laboratory. X-ray, pulmonary function tests, and skin or renal (kidney) biopsies can be used to determine the extent and severity of internal organ involvement.

There are two types of scleroderma. Localized scleroderma affects the skin in limited areas and the musculoskeletal system. Systemic sclerosis causes more widespread skin changes and may be associated with internal organ damage in the lungs, heart and kidneys. Scleroderma shares symptoms that are common with other autoimmune diseases, including but not limited to, numbness, pain or color changes in fingers, toes, cheeks, nose and ears, often brought on by cold or emotional distress (Raynaud's phenomenon), stiffness or pain in your joints and curling of your fingers, digestive problems ranging from poor absorption of nutrients to delayed movement of food due to impaired muscular activity in your intestine, sores over joints, such as your elbows and knuckles, and puffy hands and feet, particularly in the morning. It can also involve arthritis, muscle inflammation, dry eyes and dry mouth. Most patients with scleroderma have cold-induced spasms of small blood vessels in their hands or feet, known as Raynaud's phenomenon, which causes the fingers or toes to turn white or blue and may be painful. The symptoms of scleroderma vary greatly from individual to individual, and the effects of scleroderma can range from very mild to life-threatening.

Localized scleroderma has three main subtypes, which are called morphea, generalized morphea and linear scleroderma. Systemic type is the more serious type because it affects internal organ systems. Its three subtypes are called limited, diffuse and sine.

In the early months or years of disease onset, scleroderma may resemble many other connective tissue diseases, such as, but not limited to, Systemic Lupus Erythematosus, Polymyositis, and Rheumatoid Arthritis.

The most classic symptom of systemic sclerosis (scleroderma) is sclerodactyly. Initial symptoms include swollen hands, which sometimes progress to this tapering and claw-like deformity. Not everyone with scleroderma develops this degree of skin hardening. Other symptoms can include morphea, linear sclerodactyly (hardened fingers), Raynaud's syndrome, calcinosis, and telangiectasia.

Blood tests such as antinuclear antibody (ANA) tests can be used in the diagnosis of both localized and systemic scleroderma. For example, anti-centromere antibodies (ACA) and anti-Scl-70 antibodies are indicative of patients in need of treatment for systemic sclerosis (Ho et al., 2003, Arthritis Res Ther. 5:80-93); anti-topo II alpha antibody is indicative of patients in need of treatment for local scleroderma; and anti-topo I alpha antibody is indicative of patients in need of treatment for systemic scleroderma.

Several types of scleroderma and methods for diagnosing these types are recognized and well known in the art, including, but not limited to, juvenile scleroderma; localized scleroderma; Nodular Scleroderma; and Systemic scleroderma, including, but not limited to, Calcinosis, Raynaud's, Esophagus, Sclerodactyl), and Telangiectasia (CREST), limited systemic scleroderma, and diffuse systemic scleroderma. Systemic scleroderma is also known as systemic sclerosis (SSc). It may also be referred to as Progressive Systemic Sclerosis (PSSc), or Familial Progressive Systemic Sclerosis (FPSSc). Systemic sclerosis is a multisystem disorder characterized by the presence of connective tissue sclerosis, vascular abnormalities concerning small-sized arteries and the microcirculation, and autoimmune changes.

The type of systemic scleroderma known as CREST is not characterized by any skin tightening. CREST is characterized by Calcinosis (calcium deposits), usually in the fingers; Raynaud's: loss of muscle control of the Esophagus, which can cause difficulty swallowing; Sclerodactyl), a tapering deformity of the bones of the fingers: and Telangiectasia, small red spots on the skin of the fingers, face, or inside of the mouth. Typically two of these symptoms is sufficient for diagnosis of CREST. CREST may occur alone, or in combination with any other form of Scleroderma or with other autoimmune diseases.

Limited Scleroderma is characterized by tight skin limited to the fingers, along with either pitting digital ulcers (secondary to Raynaud's) and/or lung fibrosis. The skin of the face and neck may also be involved in limited scleroderma.

Diffuse Scleroderma is diagnosed whenever there is proximal tight skin. Proximal means located closest to the reference point. Proximal tight skin can be skin tightness above the wrists or above the elbows. Typically, a patient with skin tightness only between their elbows and their wrists will receive a diagnosis of either diffuse or limited systemic Scleroderma, depending on which meaning of proximal the diagnosing clinician uses. These tests are examples of tests that can be used in conjunction with the compositions and methods described herein to check for abnormalities that might exist (i.e., identify patients or patient populations in need of treatment) or to monitor side effects of drugs and check progress.

Activity of Autoimmune Diseases or Disorders

According to certain aspects, the patient or patient population being treated with B10 cell compositions described herein can have an autoimmune disease or disorder with a certain activity. The activity of an autoimmune disease or disorder can be measured by assessing multiple factors, such as, but not limited to those described above for diagnosis of autoimmune diseases and disorders. Although the above-described factors are presented in the context of certain autoimmune diseases, one or more of these factors can be used to determine the activity of other autoimmune diseases or disorders. Methods for determining activity of an autoimmune disease or disorder in a patient in relation to a scale of activity are well known in the art and can be used in connection with the pharmaceutical compositions and methods described herein.

For example, the American College of Rheumatologists Score (ACR score) can be used to determine the activity of rheumatoid arthritis of a patient or a patient population. According to this method, patients are given a score that correlates to improvement. For example, patients with a 20% improvement in factors defined by the ACR would be given an ACR20 score. This and other scoring methods may be used in combination with the methods of assessing B10 cell function described herein.

For certain other autoimmune diseases or disorders, there are several accepted methods that can be used in conjunction with the methods provided here to determine activity of an autoimmune disease or disorder. For example, SLE at several disease assessment scales, including, but not limited to, British Isle Lupus Assessment Group (BILAG), Systemic Lupus Erythematosus Disease Activity Index (SLEDI), Modified SLEDI, and Systemic Lupus Activity measure (SLAM). In general, a high activity of an autoimmune disease or disorder would be one which scores in the upper half (e.g., greater severity of disease activity) of one or more of the above scales and a low activity of an autoimmune disease or disorder would be one which scores in the lower half (e.g., less severity of disease activity) of one or more of the above scales.

Inflammatory and Allergic Diseases

Any type of inflammatory disease can be treated in accordance with the methods described herein. Non-limiting examples of inflammatory diseases include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

The methods of the invention encompass therapies that are aimed at treating diseases associated with a helper T (Th) 1-mediated inflammatory response but not diseases associated with a Th2-mediated inflammatory response. In an alternative aspect of this embodiment, the methods of the invention encompass therapies that are aimed at treating diseases associated with a Th2-mediated inflammatory response but not diseases associated with a Th1-mediated inflammatory response.

Transplantation

IL-10 is capable of inhibiting ischemia/reperfusion injury (Deng et al., 2001, Kidney int. 60:2118-28), graft-versus-host disease, and transplant-related mortality (Baker et al., 1999, Bone Marrow Transplant 23:1123-9; Holler et al., 2000, Bone Marrow Transplant 25:237-41). As such, one embodiment of the present invention involves treating transplant-associated diseases/conditions by increasing the level of IL-10 in a patient in need thereof.

In one embodiment, the levels of endogenous IL-10 are increased in a subject receiving an organ transplant by administration of a B10 cell subset such as B10 cells made by the methods described herein. In one aspect of this embodiment, the B10 cell population is isolated from the patient themselves, i.e. the subject is the donor. In another aspect of this embodiment, the B10 cell population is isolated from a donor that is not the subject. The donor of the B10 cells may be the same as the organ donor. In another embodiment, the B10 cell population is pooled from several donors.

According to certain aspects of the invention, the treatment regimen and dose used with the compositions and methods of the invention is chosen based on a number of factors including, for example, clinical manifestation that place a patient at risk for developing humoral or cellular rejection, or clinical evidence that such a rejection is developing. The terms "humoral" and "antibody-mediated" are used interchangeably herein. The criteria for assessing the risk that a patient will develop humoral or cellular rejection are established according to the knowledge and skill in the art. In one embodiment, a positive complement dependent cytotoxicity or anti-globulin enhanced complement-dependent cytotoxicity crossmatch indicates that a patient is at high risk for humoral rejection. In one embodiment, a positive crossmatch or a prior positive complement dependent cytotoxicity or anti-globulin enhanced complement dependent cytotoxicity crossmatch indicates that a patient is at an intermediate risk for humoral rejection. In one embodiment, a negative crossmatch indicates that a patient is at a low risk for humoral rejection. Similarly, there are established criteria known to those of skill in the art for establishing risk for cellular transplant rejection.

In another embodiment, a transplant recipient in need of prophylaxis against graft rejection may be identified as a patient or patient population having detectable circulating anti-HLA alloantibodies prior to transplantation. In another example, the patient or patient population is identified as having panel reactive antibodies prior to transplantation. The presence of detectable circulating anti-HLA alloantibodies in a transplant recipient post-transplantation can also be used to identify the patient or patient population in need of treatment for humoral or cellular rejection according to the invention. The patient or patient population in need of treatment for humoral or cellular rejection can also be identified according to other clinical criteria that indicate that a transplant recipient is at risk for developing humoral or cellular rejection or has already developed humoral or cellular rejection. For example, a transplant recipient in need of treatment of rejection may be identified as a patient or population in an early stage of humoral rejection, such as a latent humoral response characterized by circulating anti-donor alloantibodies. An early stage of humoral rejection may also be a silent reaction characterized by circulating anti-donor alloantibodies and C4d deposition, or a subclinical rejection characterized by circulating anti-donor alloantibodies, C4d deposition, and tissue pathology. In later stages, the recipient is identified as a patient or patient population presenting with clinical indications of humoral or cellular rejection characterized according to the knowledge and skill in the art, for example, by circulating anti-donor alloantibodies, C4d deposition, tissue pathology and/or inflammatory cell infiltrates, and graft dysfunction.

The present invention provides compositions, therapeutic formulations, methods and regimens effective to reduce the incidence, severity, or duration of graft-versus-host disease (GVHD), or a humoral or cellular rejection episode. In certain embodiments, the compositions and methods of the invention are effective to attenuate the host response to ischemic reperfusion injury of a solid tissue or organ graft. In a preferred embodiment, the B10 effector cell compositions and methods of the invention are effective to prolong survival of a graft in a transplant recipient.

The present invention encompasses grafts that are autologous, allogeneic, or xenogeneic to the recipient. The types of grafts encompassed by the invention include tissue and organ grafts, including but not limited to, bone marrow grafts, peripheral stem cell grafts, skin grafts, arterial and venous grafts, pancreatic islet cell grafts, organ transplants of the kidney, liver, lung, pancreas, thyroid, and heart, and composite tissue grafts involving tissues from multiple organ systems, including but not limited to digits, limbs, regions of the body, and facial tissues. The terms "graft" and "transplant" are used interchangeably herein. In one embodiment, the autologous graft is a bone marrow graft, an arterial graft, a venous graft or a skin graft. In one embodiment, the allograft is a bone marrow graft, a corneal graft, a kidney transplant, a pancreatic islet cell transplant, or a combined transplant of a kidney and pancreas. In one embodiment, the graft is a xenograft, preferably wherein the donor, is a pig. The compositions and methods of the present invention may also be used to suppress a deleterious immune response to a non-biological graft or implant, including but not limited to an artificial joint, a stent, or a pacemaker device.

The B10 effector cell compositions, and methods of the invention can be used to treat or prevent GVHD, or humoral or cellular rejection without regard to the particular indications initially giving rise to the need for the transplant or the particular type of tissue transplanted. However, the indications that gave rise to the need for a transplant and the type of tissue transplanted can provide a basis for a comprehensive therapeutic regimen for the treatment or prevention of GVHD and graft rejection, which comprehensive regimen comprises the B10 effector cell compositions and methods of the invention.

Therapeutic formulations and regimens of the present invention are described elsewhere for treating human subjects with other conditions. Similarly, appropriate treatment regimens can be determined by one of skill in the art for the particular patient or patient population. In particular embodiments, the treatment regimen is a pre-transplant conditioning regimen, a post-transplant maintenance regimen, or post-transplant treatment regimen for acute or chronic rejection. In certain embodiments, the particular regimen is varied for a patient who is assessed as being at a high or intermediate risk of developing a humoral or cellular immune response, compared with the regimen for a patient who is assessed as being at a low risk of developing a humoral or cellular response directed against the transplant.

In certain embodiments, the particular regimen is varied according to the stage of transplant rejection, with more aggressive therapy being indicated for patients at later stages of humoral or cellular rejection. The stages of humoral rejection may be classified according to the knowledge and skill in the art. For example, the stages of humoral rejection may be classified as one of stages I to IV according to the following criteria: Stage I Latent Response, characterized by circulating anti-donor alloantibodies, especially anti-HLA antibodies; Stage II Silent Reaction, characterized by circulating anti-donor alloantibodies, especially anti-HLA antibodies, and C4d deposition, but without histologic changes or graft dysfunction; Stage III Subclinical Rejection: characterized by circulating anti-donor alloantibodies, especially anti-HLA antibodies, C4d deposition, and tissue pathology, but without graft dysfunction; Stage IV Humoral Rejection: characterized by circulating anti-donor alloantibodies, especially anti-HLA antibodies, C4d deposition, tissue pathology, and graft dysfunction. Similarly, criteria for cellular rejection are known to those practicing in the art.

Dose response curves can be generated using standard protocols in the art in order to determine the effective amount of the compositions of the invention for use in a particular regimen, for example, in conditioning regimens prior to transplantation, and in post-transplantation regimens for prophylaxis and treatment of GVHD, or humoral or cellular rejection. In general, patients at high risk for developing humoral or cellular rejection and those already exhibiting one or more clinical indicators of rejection will require higher doses and/or more frequent doses which may be administered over longer periods of time in comparison to patients who are not at high risk or who do not exhibit any indications of active rejection.

The B10 effector cell compositions and methods of the invention can be practiced to treat or prevent GVHD, or humoral or cellular rejection, either alone or in combination with other therapeutic agents or treatment regimens. Other therapeutic regimens for the treatment or prevention of GVHD, or humoral or cellular rejection may comprise, for example, one or more of anti-lymphocyte therapy, steroid therapy, antibody depletion therapy, immunosuppression therapy, and plasmapheresis. Anti-lymphocyte therapy may comprise the administration to the transplant recipient of anti-thymocyte globulins, also referred to as thymoglobulin. Anti-lymphocyte therapy may also comprise the administration of one or more monoclonal antibodies directed against T cell and including B cell surface antigens. Examples of such antibodies include, without limitation, OKT3™ (muromonab-CD3), CAMPATH™-1H (alemtuzumab), CAMPATHT™-1G, CAMPATH™-1M, SIMULECT™ (basiliximab), and ZENAPAX™ (daclizumab).

Steroid therapy may comprise administration to the transplant recipient of one or more steroids selected from the group consisting of cortisol, prednisone, methyl prednisolone, dexamethazone, and indomethacin. Preferably, one or more of the steroids are corticosteroids, including without limitation, cortisol, prednisone, and methylprednisolone.

Antibody depletion therapy may include, for example, administration to the transplant recipient of intravenous immunoglobulin. Antibody depletion therapy may also comprise immunoadsorption therapy applied to the graft ex vivo, prior to transplantation. Immunoadsorption may be accomplished using any suitable technique, for example, protein A affinity, or antibody based affinity techniques using antibodies directed against T cell or B cell surface markers such as anti-CD3 antibodies.

Immunosuppression therapy may comprise the administration of one or more immunosuppressive agents such as inhibitors of cytokine transcription (e.g., cyclosporin A, tacrolimus), nucleotide synthesis (e.g., azathioprine, mycophenolate mofetil), growth factor signal transduction (e.g., sirolimus, rapamycin), and the T cell IL-2 receptor (e.g., daclizumab, basiliximab). In a particular embodiment, an immunosuppressant agent used in combination with the compositions and methods of the invention includes one or more of the following: adriamycin, azathioprine, busulfan, cyclophosphamide, cyclosporin A ("CyA"), cytoxin, fludarabine, 5-fluorouracil, methotrexate, mycophenolate mofetil (MOFETIL), nonsteroidal anti-inflammatories (NSAIDs), rapamycin, and tacrolimus (FK506). Immunosuppressive agents may also comprise inhibitors of complement, for example, soluble complement receptor-1, anti-C5 antibody, or a small molecule inhibitor of Cis, for example as described in Buerke et al. (J. Immunol., 167:5375-80 (2001). In one embodiment, the compositions and methods of the invention are used in combination with one or more therapeutic regimens for suppressing humoral or cellular rejection, including, without limitation, tacrolimus and mycophenolate mofetil therapy, immunoadsorption, intravenous immunoglobulin therapy, and plasmapheresis.

Diagnosis and Clinical Criteria

The present invention provides antibodies, compositions and methods for treating and preventing GVHD, and humoral or cellular rejection in human transplant recipients. The compositions and methods of the invention can be used regardless of the particular indications that gave rise to the need for a transplant. Similarly, the use of the compositions and methods of the invention for the treatment and prevention of GVHD, and humoral or cellular rejection is not limited by the particular type of tissue which is intended for transplantation or which has been transplanted.

In one embodiment, the invention provides compositions and methods for the prevention of humoral or cellular rejection in a human transplant recipient wherein the transplant recipient is identified as a patient or patient population at increased risk for developing humoral or cellular rejection. Such patients may also be referred to as "sensitized." Criteria for the identification of sensitized patients are known to skilled practitioners. Such criteria may include, for example, patients having detectable levels of circulating antibodies against HLA antigens, e.g., anti-HLA alloantibodies. Such criteria may also include patients who have undergone previous transplantations, a pregnancy, or multiple blood transfusions. Patients who are at an increased risk for humoral rejection also include those having imperfect donor-recipient HLA matching, and those transplants that are ABO-incompatible. Sensitized individuals are preferred candidates for pretreatment or conditioning prior to transplantation. Sensitized individuals are also preferred candidates for post-transplantation maintenance regimens for the prevention of humoral and cellular rejection.

In one embodiment, the B10 cell compositions and methods of the invention comprise or are used in combination with a therapeutic regimen for the treatment of an acute or chronic rejection. In particular embodiments, the rejection is characterized as Stage I, Stage II, Stage III, or Stage IV humoral or cellular rejection.

In one embodiment, the B10 cell compositions and methods of the invention comprise or are used in combination with a therapeutic regimen for the treatment of an early stage humoral rejection. In particular embodiments, the early stage humoral rejection is Stage I, II, or III rejection. Clinical indications of an early stage humoral rejection are determined according to the knowledge and skill in the art and may include, for example, the development in the patient of circulating donor-specific anti-HLA antibodies, the presence of complement markers of antibody activity such as C4d and C3d deposits in graft biopsies, and the presence of anti-HLA antibodies in graft biopsies. Other indicators of an early stage humoral rejection are known to the skilled practitioner and may include, for example, the development of anti-endothelial antibodies, especially anti-vimentin antibodies, and the development of nonclassical MHC class I-related chain A (MICA) alloantibodies. In one embodiment, the compositions and methods of the invention comprise or are used in combination with a therapeutic regimen for the treatment of humoral or cellular rejection characterized in part by graft dysfunction. In particular embodiments, the patient or patient population in need of treatment for humoral or cellular rejection is identified according to criteria known in the art for graft dysfunction. Examples of such criteria for particular types of grafts are provided in the sections that follow. In other embodiments, the patient or patient population in need of treatment for humoral or cellular rejection is identified according to other criteria that are particular to the type of tissue graft, such as histological criteria. Examples of such criteria are also provided in the sections that follow.

Bone Marrow Transplants

The compositions and methods of the invention are useful for treating or preventing GVHD, and humoral or cellular rejection in a bone marrow transplant recipient. In one embodiment, the compositions and methods of the invention comprise or are used in combination with a pre-transplant conditioning regimen. The graft may be from any suitable source, for example, cord blood stem cells, peripheral blood stem cells, or a bone marrow harvest. Peripheral blood stem cells may be harvested from donor blood following a suitable conditioning regimen. Suitable regimens are known in the art and may include, for example, administration of one or more of the following to the donor prior to harvesting the donor blood: NEUPOGEN, cytokines such as GM-CSF, low dose chemotherapeutic regimens, and chemokine therapy. The graft may be either allogeneic or autologous to the transplant recipient. The graft may also be a xenograft.

The compositions and methods of the invention are useful in a number of contexts in which there is a hematopoietic indication for bone marrow transplantation. In one embodiment, an autologous bone marrow graft is indicated for a B cell leukemia or lymphoma, preferably acute lymphoblastic leukemia ("ALL") or non-Hodgkins lymphoma. In another embodiment, the graft is an allogeneic graft and the B10 effector cell compositions and methods of the invention are used for treating graft recipients as prophylaxis against GVHD.

In one embodiment, the indication is a B cell associated autoimmune condition and the compositions and methods of the invention are used as therapy conditioning regimens. In one embodiment, the compositions of the invention are administered in combination with a chemotherapy or radiation therapy regimen, which regimen comprises a lower dose of one or more chemotherapeutic agents, or a lower dose of radiation, than the dose that is administered in the absence of the compositions of the invention. In one embodiment, the patient receives an autologous bone marrow graft subsequent to chemotherapy or radiation therapy, wherein the graft recipient is subsequently treated using the compositions and methods described herein. A patient or patient population in need of, or likely to benefit from, a bone marrow transplant is identified according to the knowledge and skill in the art. Examples of patients that may be candidates for bone marrow transplantation include patients who have undergone chemotherapy or radiation therapy for the treatment of a cancer or an autoimmune disease or disorder, and patients who are unable to clear a viral infection residing in cells of the immune system.

Liver Transplants

The compositions and methods of the invention are useful for treating or preventing GVHD, and humoral or cellular rejection in a liver transplant recipient. In particular embodiments, the rejection is an acute or a chronic refection. In one embodiment, the compositions and methods of the invention are used for the prevention of GVHD, and humoral or cellular rejection in a liver transplant recipient. In one embodiment, the compositions and methods of the invention comprise or are used in combination with a pre-transplant conditioning regimen. The liver transplant may be from any suitable source as determined according to the knowledge and skill in the art. In one embodiment, the liver is an HLA-matched allogeneic graft. In another embodiment, the liver is a xenograft, preferably from a pig donor. In one embodiment, the liver is used ex vive to filter the patient's blood, e.g., extracorporeal perfusion. Extracorporeal perfusion is a form of liver dialysis in which the patient is surgically connected to a liver maintained outside the body. This procedure is sometimes referred to as "bioartificial liver." In accordance with this embodiment, the compositions and methods of the invention are used to prevent the development of antibodies and sensitized lymphocytes against liver antigens which may contaminate the patient's blood. In one embodiment, the compositions and methods of the invention comprise an improved therapeutic regimen for the treatment and prevention of GVHD, and humoral or cellular rejection. In a particular embodiment, the compositions and methods of the invention comprise an improved therapeutic regimen, wherein the improvement lies in a decreased incidence and/or severity of complications associated with traditional immunosuppressive agents. In one embodiment, the incidence and/or severity of nephrotoxicity, hepatotoxicity, and hirsutism is reduced compared with traditional regimens relying on cyclosporinA or other calcinuerin inhibitors. In one embodiment, the incidence and/or severity of obesity, osteodystrophy, diabetes mellitus and susceptibility to bacterial and viral infections is reduced compared with traditional regimens relying on corticosteroids. In a preferred embodiment, the compositions and methods of the invention are used in combination with lower doses of one or more traditional immunosuppressive agents than the doses that are used in the absence of anti-lymphocyte antibody therapy. Preferably, the lower doses result in a decreased incidence and/or severity of one or more complications associated with the one or more traditional immunosuppressive agents.

A patient or patient population in need of, or likely to benefit from, a liver transplant is identified according to the knowledge and skill in the art. Examples of patients that may be candidates for liver transplantation include persons having one or more of the following conditions, diseases, or disorders: acute liver failure, amyloidosis, bilirubin excretion disorders, biliary atresia, Budd-Chiari syndrome, chronic active autoimmune hepatitis, cirrhosis (either associated with viral hepatitis including hepatitis B and hepatitis C, alcoholic cirrhosis, or primary biliary cirrhosis), cholangitis, congenital factor VIII or IX disorder, copper metabolism disorders, cystic fibrosis, glycogenesis, hypercholesterolemia, lipidoses, mucopolysaccharidosis, primary sclerosing cholangitis, porphyrin metabolism disorders, purine and pyrimidine metabolism disorders, and primary benign and malignant neoplasms, especially of the liver and intrahepatic bile ducts, biliary system, biliary passages, or digestive system.

The clinical criteria for the identification of a patient or patient population in need of, or likely to benefit from, a liver transplant can be determined according to the knowledge and skill in the art. Such criteria may include, for example, one or more of the following symptoms: fatigue, weight loss, upper abdominal pain, purities, jaundice, liver enlargement, discolored urine, elevated alkaline phosphatase, and gamma glutamylpeptidase activity, elevated bilirubin levels, decreased serum albumin, elevated liver-specific enzymes, low bile production, increased blood urea nitrogen, increased creatinine and/or presence of anti-neutrophil cytoplasmic antibodies (ANCA) titers, recurrent variceal hemorrhage, intractable ascites, spontaneous bacterial peritonitis, refractory encephalopathy, severe jaundice, exacerbated synthetic dysfunction, sudden physiologic deterioration, and fulminant hepatic failure.

Kidney (Renal) Transplants

The compositions and methods of the invention are useful for treating or preventing GVHD, and humoral or cellular rejection in a renal transplant recipient. As used herein, the term "renal transplant" encompasses the transplant of a kidney and the combined transplant of a kidney and a pancreas. In particular embodiments, the rejection is characterized as acute rejection or chronic rejection.

In one embodiment, the compositions and methods of the invention comprise or are used in combination with a pre-transplant conditioning regimen. In one embodiment, a single dose of one or more of the compositions of the present invention is effective in the patient or patient population. In another embodiment, multiple doses of one or more of the compositions of the invention are effective in the patient or patient population. In one embodiment, a single dose of one or more of the compositions of the present invention is administered in combination with one or more immunosuppressive agents and is effective in the patient or patient population.

In certain embodiments, the compositions and methods of the invention are for treating or preventing GVHD and graft rejection in a patient having received a renal transplant. In one embodiment, the patient has not yet exhibited clinical signs of rejection. In a related embodiment, the compositions and methods of the invention comprise or are used in combination with a maintenance regimen for the prevention of graft rejection in the transplant recipient. In one embodiment, the compositions and methods of the invention are for the treatment of subclinical humoral rejection. In a related embodiment, the patient or patient population in need of treatment for a subclinical humoral rejection is indicated by the detection of Cd4 deposition or cellular infiltration in a biopsy from the graft, or by the detection of circulating anti-HLA antibodies. In one embodiment, the compositions and methods of the invention are for the treatment of subclinical cellular rejection.

In one embodiment, the compositions and methods of the invention comprise or are used in combination with a therapeutic regimen for the treatment of an acute or chronic rejection episode in a transplant recipient. In one embodiment, the patient or patient population in need of treatment for an acute or chronic rejection episode is identified by the detection of one or more clinical indicators of rejection. In specific embodiments, the one or more clinical indicators of rejection are detected one to six weeks post-transplantation. In one embodiment, the one or more clinical indicators of rejection are detected 6, 12, 18, 24, 36, 48, or 60 months post-transplantation. In a preferred embodiment, the acute rejection is biopsy-confirmed acute humoral or cellular rejection.

In one embodiment, one or more of the compositions of the invention comprise a therapeutic regimen for the treatment of acute rejection. In a particular embodiment, the therapeutic regimen further comprises one or more of the following: plasmapheresis, tacrolimus/mycophenolate, intravenous immunoglobulin, and immunoadsorption with protein A. In one embodiment, the patient has been on an immunosuppressive protocol prior to the development of the rejection. In a particular embodiment, the immunosuppressive protocol includes one or more of cyclosporine, azathioprine, and steroid therapy.

Clinical indicators of acute humoral and cellular rejection are known in the art and include, for example, a sudden severe deterioration of renal function, the development of oliguria, and compromised renal perfusion. Additional indicators include, for example, inflammatory cells in peritubular capillaries on biopsy and circulating donor-specific alloantibodies. In one embodiment, the patient presents with one or more of the following diagnostic criteria for a humoral rejection of a renal allograft: (1) morphological evidence of acute tissue injury; (2) evidence of antibody action, such as C4d deposits or immunoglobulin and complement in arterial fibrinoid necrosis; and (3) detectable circulating antibodies against donor HLA antigens or donor endothelial antigens. In one embodiment, the patient presents with all three of the above diagnostic criteria.

In one embodiment, the patient presents with one or more of the diagnostic criteria for acute humoral or cellular rejection and the compositions of the present invention are used in combination with one or more of the following immunosuppressive agents to treat acute rejection: intravenous immunoglobulin, anti-thymocyte globulins, mycophenolate mofetil, or tacrolimus. In another embodiment, the compositions of the invention are used in combination with one or more immunosuppressive agents and a procedure for the removal of alloantibodies from the patient, such as plasmapheresis or immunoadsorption.

In one embodiment, the compositions and methods of the invention comprise or are used in combination with a therapeutic regimen for the treatment of chronic renal allograft rejection. In one embodiment, one or more of the compositions of the invention are used alone or in combination with one or more immunosuppressive agents, including for example, monoclonal antibodies, tacrolimus, sirolimus, and mizoribin. In a preferred embodiment, one or more of B10 effector cell compositions of the invention are used in combination with tacrolimus, mycophenolate, or other appropriate therapeutics.

Clinical indicators of chronic rejection in the kidneys are known in the art and may include, for example, arterial intiamal fibrosis with intimal mononuclear cells (chronic allograft vasculopathy), duplication of the glomerular basement membranes (chronic allograft glomerulopathy), lamination of the peritubular basement membrane, C4d deposition in peritubular capillaries, inflammatory cell infiltrates and immunopathology, and detectable circulating donor HLA-reactive antibodies. In a preferred embodiment, the compositions and methods of the invention comprise or are used in combination with a therapeutic regimen to treat chronic rejection before graft lesions develop.

In another embodiment, the patient or patient population in need of treatment is identified as having one or more clinical indicators of transplant glomerulopathy. In a related embodiment, the compositions of the invention comprise or are used in combination with a therapeutic regimen comprising one or more therapeutic agents. In a preferred embodiment, the therapeutic regimen is effective to stabilize renal function and inhibit graft rejection. In a particular embodiment, the one or more therapeutic agents include angiotensin converting enzyme (ACE) inhibitors and/or receptor antagonists, intra-venous immunoglobulin, anti-thymocyte globulins, mycophenolate mofetil, or tacrolimus.

Preferably, the B10 effector cells of the invention are used in combination with mycophenolate mofetil and tacrolimus, with or without other therapeutic agents. Plasmapheresis and other treatments may also be used as part of the therapeutic regimen.

A patient or patient population in need of, or likely to benefit from, a renal transplant is identified according to the knowledge and skill in the art. Examples of patients that may be candidates for renal transplantation include patients diagnosed with amyloidosis, diabetes (type I or type II), glomerular disease (e.g., glomerulonephritis), gout, hemolytic uremic syndrome, HIV, hereditary kidney disease (e.g., polycystic kidney disease, congenital obstructive uropathy, cystinosis, or prune bell syndrome), other kidney disease (e.g., acquired obstructive nephropathy, acute tubular necrosis, acute interstitial nephritis), rheumatoid arthritis, systemic lupus erythematosus, or sickle cell anemia. Other candidates for renal transplant include patients having insulin deficiency, high blood pressure, severe injury or burns, major surgery, heart disease or heart attack, liver disease or liver failure, vascular disease (e.g., progressive systemic sclerosis, renal artery thrombosis, scleroderma), vesicoureteral reflux, and certain cancers (e.g., incidental carcinoma, lymphoma, multiple myeloma, renal cell carcinoma, Wilms tumor). Other candidates for renal transplant may include, for example, heroin users, persons who have rejected a previous kidney or pancreas graft, and persons undergoing a therapeutic regimen comprising antibiotics, cyclosporin, or chemotherapy. The clinical criteria for the identification of a patient or patient population in need of, or likely to benefit from, a kidney transplant can be determined according to the knowledge and skill in the art. Such criteria may include, for example, one or more of the following: urinary problems, bleeding, easy bruising, fatigue, confusion, nausea and vomiting, loss of appetite, pale skin (from anemia), pain in the muscles, joints, flanks, and chest, bone pain or fractures, and itching.

Cardiac Transplants

The compositions and methods of the invention are useful for treating or preventing GVHD, and humoral or cellular rejection in a cardiac transplant recipient. In particular embodiments, the rejection is acute or a chronic rejection. In one embodiment, the compositions and methods of the invention comprise or are used in combination with a pre- or post-transplant conditioning regimen.

In certain embodiments, the compositions and methods of the invention comprise or are used in combination with a therapeutic regimen for the treatment of acute humoral or cellular rejection in a cardiac transplant recipient. In a particular embodiment, the therapeutic regimen further comprises one or more of the following: plasmapheresis, intravenous immunoglobulin, and antibody therapy. The patient or patient population in need of treatment for an acute humoral rejection is identified by the detection of one or more of the clinical indications of acute humoral rejection. Examples of clinical indicators of acute humoral rejection may include one or more of the following: hemodynamic dysfunction, defined by shock, hypotension, decreased cardiac output, and a rise in capillary wedge or pulmonary artery pressure. In a particular embodiment, the acute humoral rejection is diagnosed within 6, 12, 18, 24, 36, 48, or 60 months post-transplantation.

In one embodiment, the compositions and methods of the invention comprise or are used in combination with a therapeutic regimen for the prevention of humoral or cellular rejection in a cardiac transplant recipient. In one embodiment, the transplant recipient in need of prophylaxis against rejection is identified as a patient or patient population having one or more of the following risk factors: female sex, cytomegalovirus seropositivity, elevated response to panel reactive antibodies, positive pre- and/or post-transplant crossmatch, and pre-sensitization with immunosuppressive agents.

In one embodiment, the compositions and methods of the invention are for the treatment or prevention of graft deterioration in a heart transplant recipient. In one embodiment, the transplant recipient in need of treatment for, or prophylaxis against, graft deterioration is identified as a patient or patient population having one or more of the following clinical indications of humoral or cellular rejection: deposition of immunoglobulin, C1q, C3, and/or C4d in capillaries, evidence of CD68-positive cells within capillaries, and evidence of infiltration of the graft by inflammatory cells upon biopsy. In one embodiment, the compositions of the present invention are used in combination with one or more of the following immunosuppressive agents to treat graft deterioration in a heart transplant recipient: intravenous immunoglobulin, anti-thymocyte globulins, monoclonal antibodies, mycophenolate mofetil, or tacrolimus. In another embodiment, the B10 effector cell compositions of the invention are used in combination with one or more immunosuppressive agents and a procedure for the removal of alloantibodies from the patient, such as plasmapheresis or immunoadsorption.

In one embodiment, the compositions and methods of the invention comprise or are used in combination with a therapeutic regimen for the treatment of chronic cardiac rejection, preferably chronic allograft vasculopathy, also referred to as transplant coronary artery disease. In another embodiment, the compositions and methods of the invention comprise or are used in combination with a therapeutic regimen for the prevention of transplant coronary artery disease in a patient or patient population at risk. The criteria for identifying a patient or patient population at risk of developing transplant coronary artery disease are known in the art and may include, for example, patients having poorly matched transplants, patients who develop circulating anti-HLA antibodies, and patients who develop one or more clinical indications of humoral or cellular rejection early after cardiac transplant.

A patient or patient population in need of, or likely to benefit from a heart transplant is identified according to the knowledge and skill in the art. Examples of patients that may be candidates for heart transplantation include those who have been diagnosed with any of the following diseases and disorders: coronary artery disease, cardiomyopathy (noninflammatory disease of the heart), heart valve disease with congestive heart failure, life-threatening abnormal heart rhythms that do not respond to other therapy, idiopathic cardiomyopathy, ischemic cardiomyopathy, dilated cardiomyopathy, ischemic cardiomyopathy, and congenital heart disease for which no conventional therapy exists or for which conventional therapy has failed.

The clinical criteria for the identification of a patient or patient population in need of, or likely to benefit from, a heart transplant can be determined according to the knowledge and skill in the art. Such criteria may include, for example, one or more of the following: ejection fraction less than 25%, intractable angina or malignant cardiac arrhythmias unresponsive to conventional therapy, and pulmonary vascular resistance of less than 2 Wood units. In addition, the patient or patient population in need of a heart transplant may be identified by performing a series of tests according to the knowledge and skill in the art. Such tests include, for example, resting and stress echocardiograms, EKG, assay of blood creatinine levels, coronary arteriography, and cardiopulmonary evaluation including right- and left-heart catheterization.

Lung Transplant

The compositions and methods of the invention are useful for treating or preventing GVHD, and humoral or cellular rejection in a lung transplant recipient. In particular embodiments, the refection is characterized as an acute or a chronic rejection. In one embodiment, the compositions and methods of the invention comprise or are used in combination with a pre-transplant conditioning regimen. A patient or patient population in need of, or likely to benefit from, a lung transplant is identified according to the knowledge and skill in the art. Examples of patients that may be candidates for lung transplantation include patients having one of the following diseases or conditions: bronchiectasis, chronic obstructive pulmonary disease, cystic fibrosis, Eisenmenger syndrome or congenital heart disease with Eisenmenger syndrome, emphysema, eosinophilic granuloma of the lung, or histiocytosis X, inhalatiodbum trauma, lymphangioleiomyomatosis (LAM), primary pulmonary hypertension, pulmonary fibrosis (scarring of the lung), or sarcoidosis.

The clinical criteria for the identification of a patient or patient population in need of, or likely to benefit from, a lung transplant can be determined according to the knowledge and skill in the art. Such criteria may include, for example, one or more of the following: chronic obstructive pulmonary disease (COPD) and alphal-antitrypsin deficiency emphysema characterized by one or more of the following indicators: postbronchodilator FEV1 of less than 25% predicted, resting hypoxemia, i.e., $PaO_2$ of less than 55-60 mm Hg, hypercapnia, secondary pulmonary hypertension, a rapid rate of decline in FEV1, or life-threatening exacerbations; cystic fibrosis characterized by one or more of the following indicators: postbronchodilator FEV1 of less than 30% predicted, resting hypoxemia, hypercapnia, or increasing frequency and severity of exacerbations; idiopathic pulmonary fibrosis characterized by one or more of the following indicators: vital capacity (VC) and TLC of less than 60-65% predicted, and resting hypoxemia; secondary pulmonary hypertension characterized by clinical, radiographic, or physiologic progression while on medical therapy; primary pulmonary hypertension characterized by one or more of the following indicators: NYHA functional class III or IV, mean right atrial pressure of greater than 10 mm Hg, mean pulmonary arterial pressure of greater than 50 mm Hg, cardiac index of less than 2.5 $L/min/m^2$, and failure of therapy with long-term prostacyclin infusion.

Treatment of Subjects Receiving Biologics

Methods of treating subjects receiving recombinant, therapeutic or xenogeneic protein(s) are also provided. The methods include administering a therapeutically effective amount of the B10 cells described herein to a subject in need of treatment for a genetic, transplantation, allergy, inflammation, or autoimmune disorder. In particular the B10 cells may be co-administered with a biologic or other therapeutic to which a subject may develop or has developed anti-drug antibodies.

As the number of biologic therapies that reach the clinics continues to increase, there is an increasing appreciation that recipients frequently develop immune responses to these drugs, which has a potential clinical impact on drug efficacy. Immune responses to biologics are generally monitored by detection and characterization of anti-drug antibodies (ADA) and assessing ADA associations with drug exposure, efficacy and safety. The detection of ADA does not necessarily mean that there will be clinical consequences. There are, however, an increasing number of examples where ADA can challenge drug efficacy and patient safety.

Thus the B10 cell compositions may be used in combination with (co-administration, provided before or after) a biologic therapy to avoid production of ADA.

Assessing B10 Cell Function

Methods of assessing the B10 cell function in a subject are also provided herein. The methods include harvesting B cells from a subject as discussed above for the methods of expanding B cells ex vivo and culturing the cells in the presence of a CD40 agonist and IL-21. Any of the methods for expanding B cells described herein may be utilized to assess B10 cell function in the subject. After culturing with IL-21, the cells are then assayed to determine if the cells are capable of producing IL-10. The percentage of cells in the culture capable of making IL-10 and/or the amount of IL-10 produced by the cells may be determined. The determination may be made either after culturing with IL-21 or after culture with another stimulatory molecule or combination of molecules such as an antigen or LPS. The determination of the percentage of cells producing IL-10 or the amount of IL-10 being produced may be determined by any method available to one of skill in the art.

The amount of IL-10 or percentage of cells producing IL-10 may be determined and compared to a control. Suitably the control is a normal control comprising B cells from a healthy donor treated similarly to the cells obtained from the subject. Alternatively the control may be represented by a numeric range over which healthy donor cells are expected to fall. The B10 cell function of the subject may be normal, overactive or deficient as compared to a healthy donor. If B10 cell function is not normal, the method may be used to diagnose the subject or indicate that the subject either has or is likely to have a disease or condition affecting B10 cell function.

The following examples are meant only to be illustrative and are not meant as limitations on the scope of the invention or of the appended claims. All references cited herein are hereby incorporated by reference in their entireties.

EXAMPLES

Figure 5:
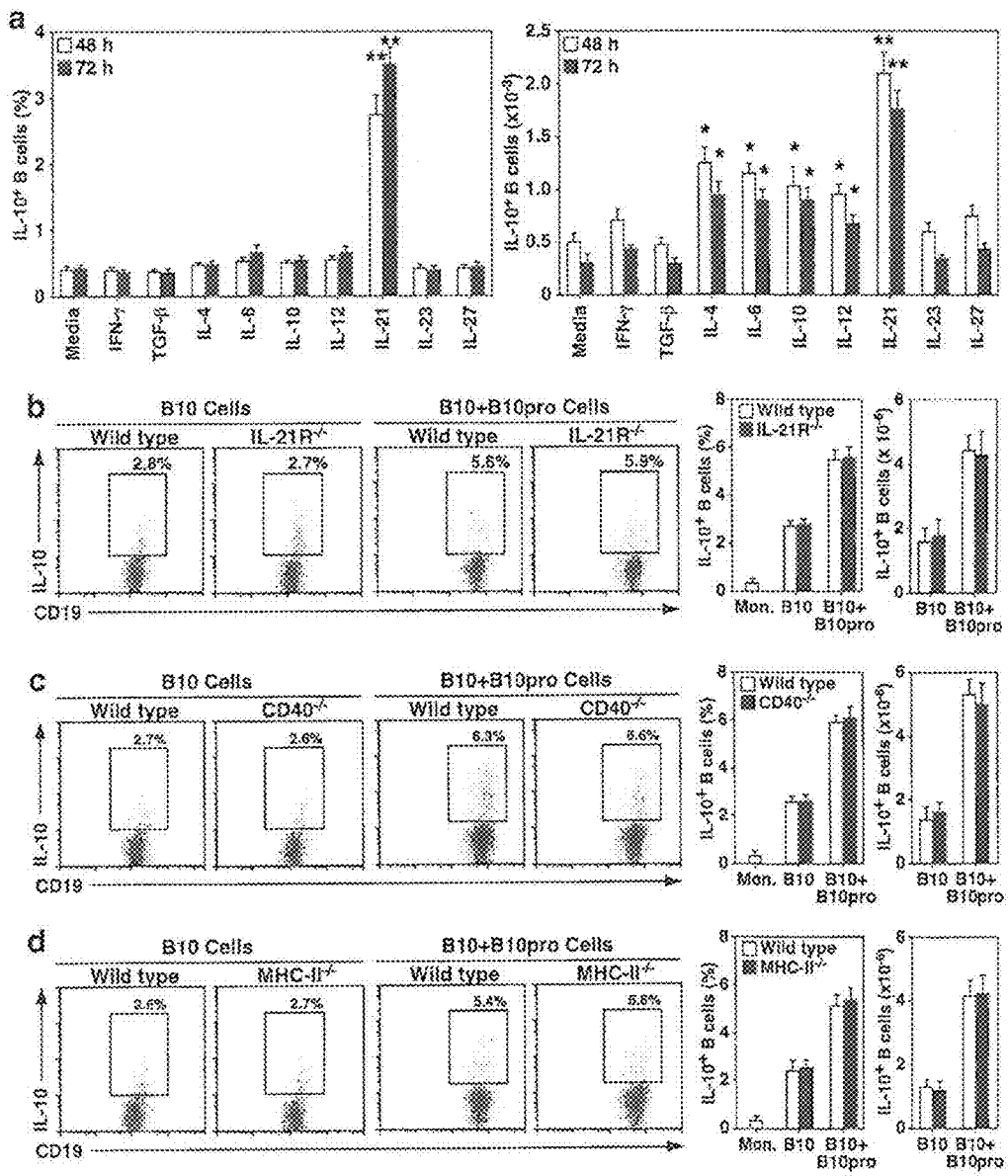
FIG. 5 presents a set of data showing that IL-21 induces regulatory B10 cell function.

To identify signals that regulate B10 cells in vivo, purified B cells were cultured with cytokines known to influence B cell function. Stimulation with IL-21, but not IL-4, -6, -10, -12, -23 or -27, induced 2.7- to 3.2-fold higher B10 cell frequencies and 4.4- to 5.3-fold more IL-10 secretion ($p<0.01$) at 48 and 72 h. respectively, while interferon-γ (IFN-γ) or transforming growth factor-β (TGF-β) reduced IL-10$^+$ B cell frequencies by 56% ($p<0.05$; FIG. 1A). In fact, IL-21 induced B10 cells to produce IL-10 without a need for in vitro stimulation (FIG. 5A) and induced B cell IL-10 secretion at levels similar to lipopolysaccharide (LPS) stimulation (FIG. 1A). IL-21 also induced a 3-fold increase in IL-10$^+$ B cells within the spleen CD1d$^{hi}$CD5$^+$ B cell subset that is enriched for B100pro and B10 cells, but it did not induce significant numbers of IL-10$^+$ B cells among the CD1d$^{lo}$CD5$^-$ subset (FIG. 1B). There was little if any detectable B cell division in the 48 or 72 h assays when the cells were cultured with cytokines alone. Even when mitogens such as anti-IgM antibody or LPS were added to induce B cell proliferation, there was still little proliferation at 48 h, although B10 cells are the most proliferative cells at 72 h. IL-21 did not promote B10 cell survival, but instead accelerated the apoptosis of non-B10 cells while B10 cells were predominantly spared. The net result was that B10 cell numbers were preferentially increased by IL-21 relative to other cytokines. Consistent with this, IL-21 induces either B cell apoptosis or differentiation in a context-dependent manner, driving the in vitro differentiation and expansion of more completely activated B cells. See Spolski, R. & Leonard, W. J. Interleukin-21: basic biology and implications for cancer and autoimmunity. Annu Rev Immunol 26, 57-79 (2008) and Ozaki, K. et al. Regulation of B cell differentiation and plasma cell generation by IL-21, a novel inducer of Blimp-1 and Bcl-6. J. Immunol. 173, 5361-5371 (2004). IL-21 is also known to be a potent inducer of T cell IL-10 production, and T cell-derived IL-21 plays multiple important roles in B cell effector function. Both B10 and non-B10 cells expressed cell surface IL-21 receptor (IL-21R) at similar levels (FIG. 1C). Despite this, ex vivo B10 and B10+B10pro cell and CD1d$^{hi}$CD5$^+$ B cell numbers were similar in IL-21R-deficient (IL-21R$^{-/-}$), wild type, MHC-II$^{-/-}$ and CD40$^{-/-}$ mice (FIG. 5B-D). However, IL-21R expression was required for B10 cell expansion following myelin oligodendrocyte glycoprotein peptide (MOG$_{35-55}$) immunizations to induce EAE (FIG. 1D). Thus, IL-21R-generated signals induced B cell IL-10 secretion in vivo and in vitro and were required for B10 cell expansion in vivo.

Figure 2:
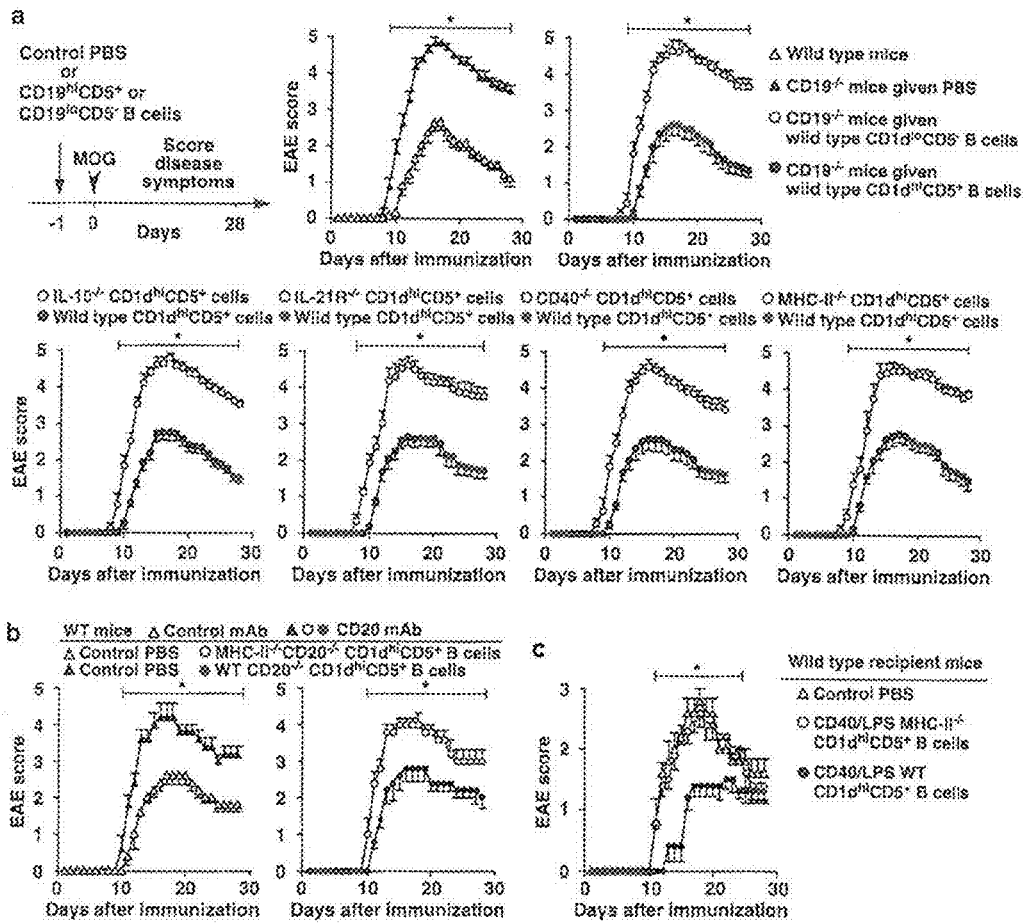
FIG. 2 is a set of data which demonstrate that B10 cells require IL-10, IL-21R, CD40, and MHC-II expression to regulate EAE severity.

Whether B10 cells require IL-21 to induce their regulatory function in vivo was determined by the adoptive transfer of IL-21R$^{-/-}$ B cells into CD19$^{-/-}$ mice before the induction of EAE by MOG$_{35-55}$ immunization. Because CD19$^{-/-}$ mice are B10 cell-deficient (FIG. 1d), their EAE disease severity is worse (FIG. 2A). The adoptive transfer of wild type CD1d$^{hi}$CD5$^+$ B cells normalized EAE severity in CD19$^{-/-}$ mice. By contrast, the transfer of CD1d$^{hi}$CD5$^+$ B cells from IL-10$^{-/-}$ or IL-21$^{-/-}$ mice or wild type CD1d$^{lo}$CD5$^-$ non-B10 cells did not alter disease. Because CD4$^+$ T cells are a major source of IL-21, we determined whether cognate B10-T cell interactions also controlled B10 cell-mediated suppression of EAE. The transfer of CD1d$^{hi}$CD5$^+$ B cells from MHC-II$^{-/-}$ or CD40$^{-/-}$ mice into CD19$^{-/-}$ mice before MOG immunizations did not reduce EAE disease severity (FIG. 2A, bottom right two panels). CD1d$^{lo}$CD5$^-$ B cells from IL-21R$^{-/-}$, CD40$^{-/-}$ or MHC-II$^{-/-}$ mice were also without effect. EAE is also exacerbated in wild type mice depleted of mature B cells by CD20 mAb. However, transfer of CD1d$^{hi}$CD5$^+$ B cells from CD20$^{-/-}$ mice but not MHC-II$^{-/-}$CD20$^{-/-}$ mice normalized disease severity in this model, and CD1d$^{lo}$CD5$^-$ B cells from CD20$^{-/-}$ or MHC-II$^{-/-}$CD20$^{-/-}$ mice were without effect (FIG. 2B). Similarly, the adoptive transfer of in vitro activated CD1d$^{hi}$CD5$^+$ B cells from wild type mice significantly reduced EAE disease severity in wild type mice, whereas activated MHC-II$^{-/-}$ CD1d$^{hi}$CD5$^+$ or wild type CD1d$^{lo}$CD5$^-$ B cells had no effect (FIG. 2C). Thus, regulatory B10 cell function required IL-10 expression, IL-21R signaling, as well as CD40 and MHC-II interactions, thereby potentially explaining antigen-specific B10 cell effector function.

Figure 3:
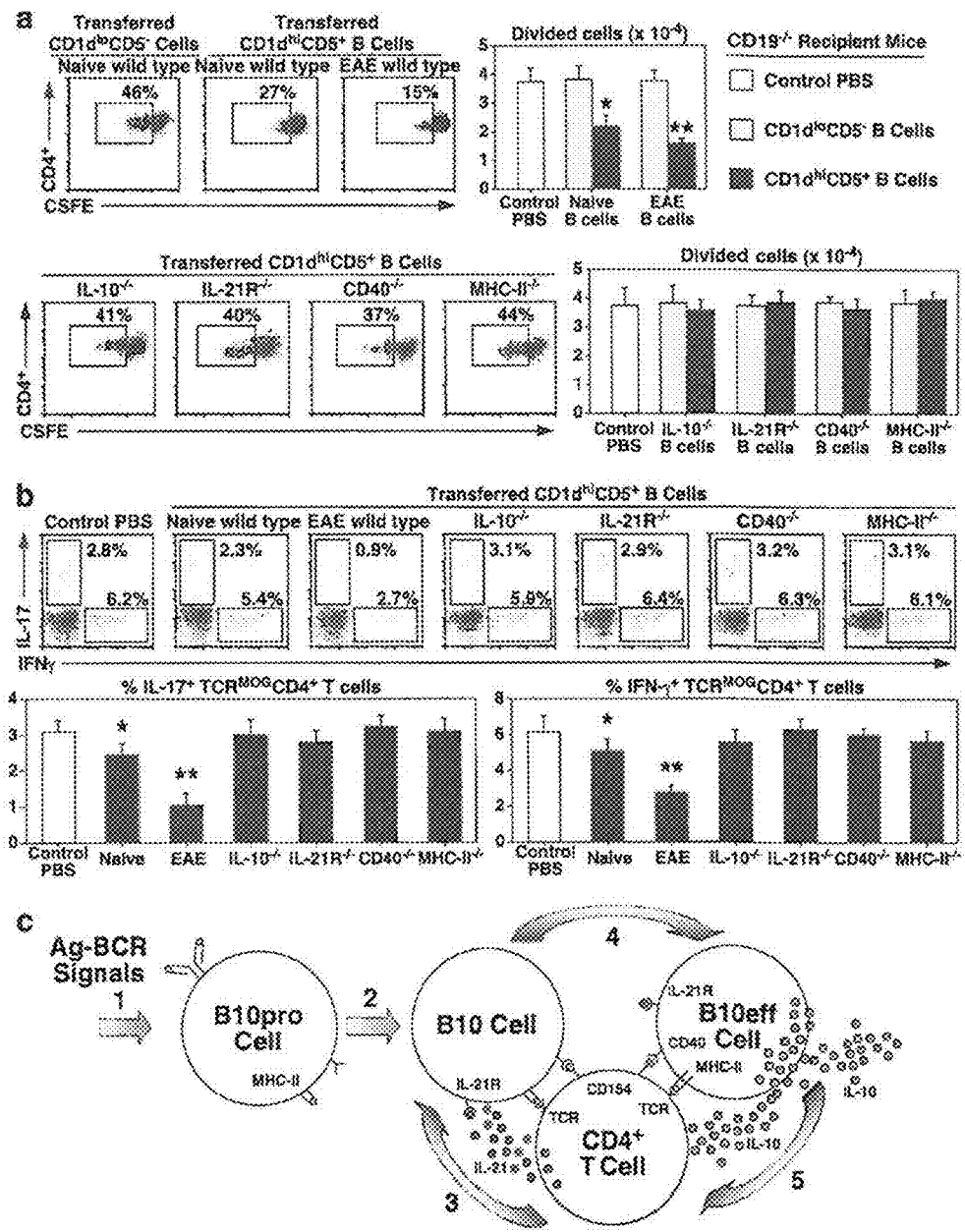
FIG. 3 is a set of data showing B10 cell expansion and regulation of T cell-mediated autoimmunity.
Figure 6:
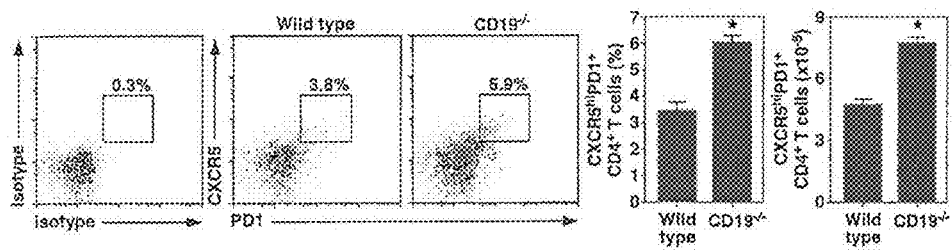
FIG. 6 is a set of dot blots and bar graphs showing that T follicular helper cells are present in $CD19^{-/-}$ mice. Representative flow cytometry analysis of $CXCR5^{hi}PD1^+$ cells among spleen $CD4^+$ T cells from wild type and $CD19^{-/-}$ mice. Bar values represent mean (±SEM) $CXCR5^{hi}PD1^+$ cell frequencies among $CD4^+$ T cells from three mice. Significant differences between sample means are indicated: *, p<0.05.

IL-10 produced by activated CD1d$^{hi}$CD5$^+$ B cells inhibits antigen-specific CD4$^+$ T cell IFN-γ and TNF-α expression in vitro. To determine whether cognate B10-T cell interactions regulate antigen-specific T cell proliferation in vivo, 110 cell function was assessed in MOGO$_{35-55}$-immunized CD19$^{-/-}$ mice following the adoptive transfer of dye-labeled CD4$^+$ T cells from transgenic mice expressing antigen receptors (TCR$^{MOG}$) specific for MOG$_{35-55}$ peptide. See Bettelli, E. et al. Myelin oligodendrocyte glycoprotein-specific T cell receptor transgenic mice develop spontaneous autoimmune optic neuritis. J. Exp. Med. 197, 1073-1081 (2003). CD1d$^{hi}$CD5$^+$ B cells from naïve wild type mice significantly reduced TCR$^{MOG}$ CD4$^+$ T cell proliferation as measured by in vivo dye dilution (FIG. 3A). CD1d$^{lo}$CD5$^-$ B cells obtained from mice with EAE were even more potent inhibitors of T cell proliferation, while CD1d$^{lo}$CD5$^-$ B cells from wild type mice or CD1d$^{hi}$CD5$^+$ B cells from IL-10$^{-/-}$, IL-21R$^{-/-}$, CD40$^{-/-}$, or MHC-II$^{-/-}$ mice were without effect. CD1d$^{hi}$CD5$^+$ B cells from naïve or antigen-experienced wild type mice also significantly reduced TCR$^{MOG}$ CD4$^+$ T cell IFN-γ and IL-17 production in MOG$_{35-55}$-immunized CD19$^{-/-}$ mice, while CD1d$^{hi}$CD5$^+$ B cells from IL-10$^{-/-}$, IL-21R$^{-/-}$, CD40$^{-/-}$ or MHC-II$^{-/-}$ mice did not (FIG. 3B). The ability of B10 cells to inhibit T cell IL-17 production is particularly important since pathogenic T$_H$17 T cells induce EAE and can produce IL-21. The majority of T follicular helper cells isolated from mice with MOG$_{35-55}$s-induced EAE also express IL-21, and CD19$^{-/-}$ mice have T follicular helper cells (FIG. 6). Thus, B10 and T cells may require intimate interactions during reciprocal IL-10 and IL-21 production to optimally regulate antigen-specific disease (FIG. 3C).

Although T follicular helper cells are a likely source of IL-21, there are currently no indications that B10 cells are germinal center constituents and most data argue against this. First, B10 cell BCRs are predominantly germline and contain modest frequencies of IgV$_H$ and IgV$_L$ mutations. Maseda, D. et al. Regulatory B10 cells differentiate into antibody-secreting cells after transient IL-10 production in vivo. J. Immunol. 188, 1036-1048 (2012). Second, B10 cell numbers expand early during the induction of EAE, prior to the generation of germinal centers. Matsushita, T., Horikawa, M., Iwata, Y. & Tedder, T. F. Regulatory B cells (B10 cells) and regulatory T cells have independent roles in controlling EAE initiation and late-phase immunopathogenesis. J. Immunol. 185, 2240-2252 (2010). Third, B310 cell GL-7 expression resembles spleen follicular B cells and not GL-7$^{high}$ germinal center B cells. Matsushita, 2010. Furthermore, a hallmark of transgenic mice with dramatically expanded B10pro-+B10 cell numbers is the absence of germinal centers and little if any B cell isotype switching, even after immunizations. Poe, J. C. et al. Amplified B lymphocyte CD40 signaling drives regulatory B10 cell expansion in mice. PLoS ONE 6, e22464 (2011). B10 cells in these mice are also located throughout both the marginal zone and follicular areas of the spleen.

To verify that T cell-derived IL-21 and CD40 signals drive B10 cell expansion and IL-10 production, B cells were cultured using conditions to promote mouse B10 cell expansion in vivo and B cell expansion in vitro. See Poe, 2011 and Nojima, T. et al. In-vitro derived germinal centre B cells differentially generate memory B or plasma cells in vivo. Nature Comm. 2, 465 (2011). B cells were cultured on monolayers of NIH-3T3 cells expressing the T cell ligand for CD40 (CD154) and BLyS in the presence of IL-4 for 4 days to induce B10pro cell maturation into IL-10-competent B10 cells. The B cells were then cultured on fresh NIH-3T3-CD154/BLyS cells with exogenous IL-21 for 5 days, which were all essential to optimally expand B10 cells and induce IL-10 production (FIG. 4A). After the 9 day culture period, B cell and 10 cell numbers were increased by 25,000- and 4,000,000-fold, respectively, with 38% of the B cells actively producing IL-10 (FIG. 4B). The vast majority of IL-10$^+$ B cells in the cultures expressed CD5 (FIG. 4C), facilitating their purification and underscoring the dramatic effect of IL-21 on B10 cell numbers in vitro.

In vitro-expanded CD5$^+$ B10 cells retained their regulatory function. The transfer of CD5$^+$ B10 cells dramatically reduced EAE disease severity in wild type mice, even when given after the appearance of disease symptoms, while CD5⁻ B cells were without effect (FIG. 4D). Although the in vitro expansion of B10 cells required both IL-21R and CD40 signals, MHC-II expression was not required (FIG. 4E). However, in vitro-expanded MHC-II$^{-/-}$CD5$^+$ B10 cells and IL-10$^{-/-}$ CD5$^+$ B cells did not regulate EAE disease severity (FIG. 4F), further documenting a requirement for IL-10 and cognate interactions in the regulation of T cell-mediated disease. B10 cells did not expand during in vitro cultures of B cells from CD19$^{-/-}$ mice or MD4 transgenic mice that have a fixed BCR specific for egg lysozyme (FIG. 4E), further underscoring the importance of BCR specificity and signaling in B10 cell generation. Otherwise, in vitro-expanded B10 effector cells were potent regulators of both disease initiation and progression.

Figure 4:
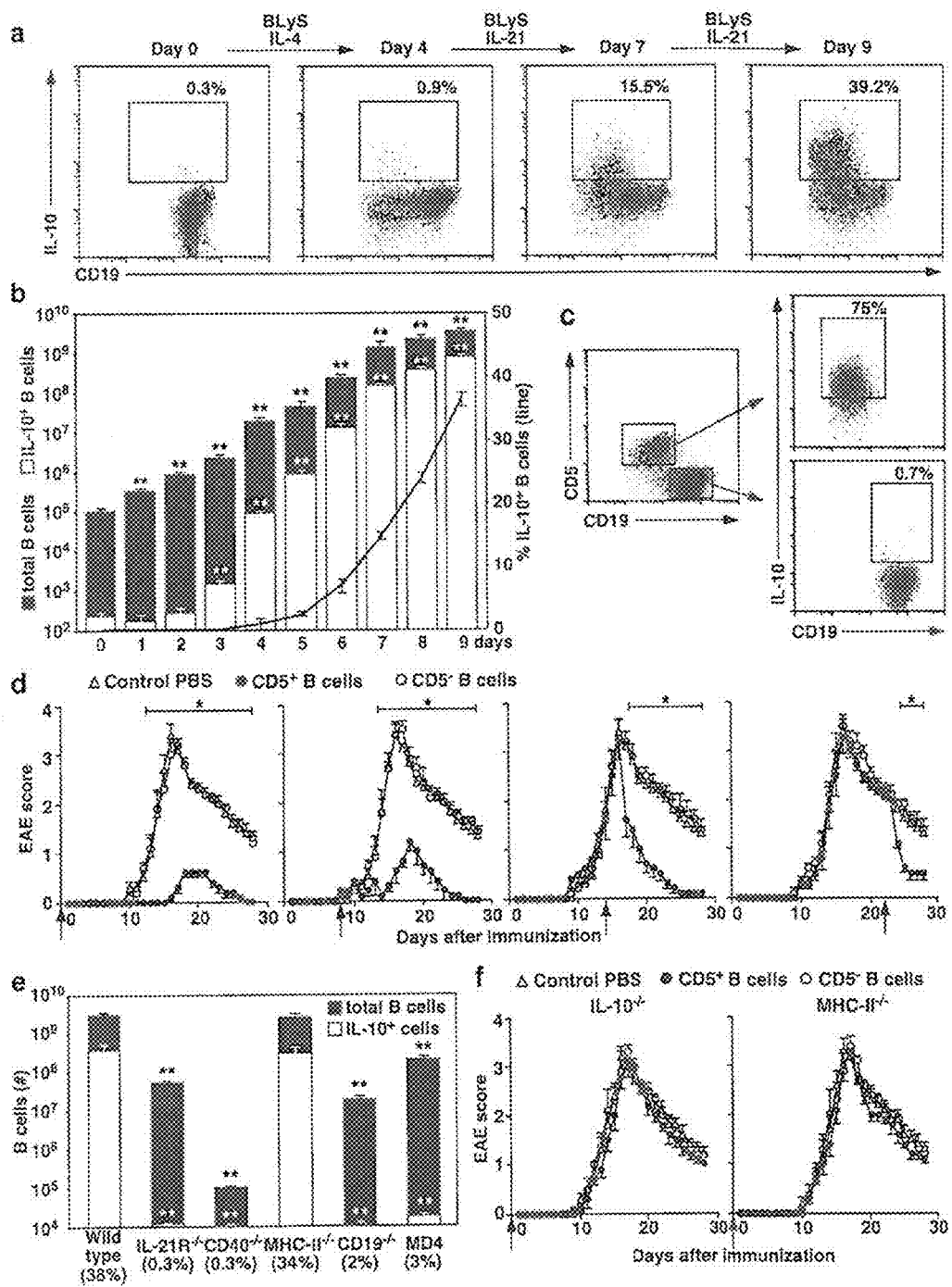
FIG. 4 is a set of data showing that IL-21 drives ex vivo regulatory B10 cell expansion.

This study demonstrates that CD40 signals induce B10pro cell acquisition of IL-10 competence with IL-21 driving B10 cell expansion and effector cell generation. These critical checkpoints in B10 cell development may lead to localized IL-10 production that blunts antigen-specific T cell responses during cognate interactions (FIG. 3C) without untoward immunosuppression. Transient IL-10 production by B10 cells in vivo may further restrict the effects of IL-10 secretion. B10 effector cells may also regulate T cell responses to autoantigens in addition to MOG once inflammation and tissue destruction are initiated by MOG$_{35-55}$ immunization. Since human and mouse B10 cells are also potent regulators of macrophage and dendritic cell function, T cell induction of B10 effector cells may also contribute to EAE resolution by restraining monocyte and dendritic cell activation. These collective results may explain in part why EAE is exacerbated in the absence of IL-21 signaling. By contrast, TGF-β and IFN-γ may counterbalance B10 cell expansion in vivo based on the current in vitro findings (FIG. 1A). Regulatory T cells provide an independent layer of regulation during EAE since their expansion, accumulation in the central nervous system, and suppressive activity are normal when B10 cells are absent. The in vitro recapitulation of these collective signals induced a several million-fold expansion of B10 cells and their functional maturation into potent B10 effector cells that reversed established autoimmune disease (FIG. 4). In addition to BCR specificity, MHC-II expression remained an important checkpoint for B10 effector cell regulatory function during EAE (FIG. 4F), as first described for regulatory type II monocytes. Since autoimmunity has multigenic origins and autoantigens vary between patients and disease, in vitro expansion of the rare pool of human blood B10pro and B10 effector cells may provide a potent future immunotherapy for individuals with severe autoimmune disease.

Human B10 Cell Expansion in Vitro.

Figure 7:
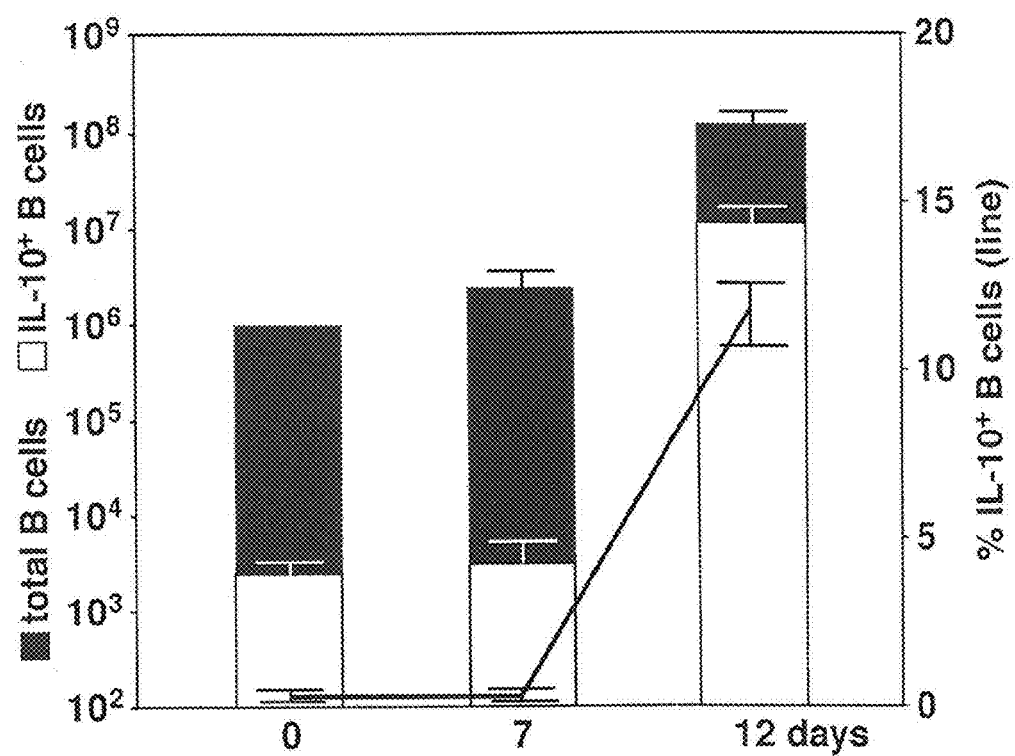
FIG. 7 is a graph showing the total number of B cells and B10 cells after the indicated time in culture and the amount of IL-10 produced by the culture. Purified human blood B cells were cultured on NIH-3T3-mCD154/hBLyS cell monolayers with exogenous human IL-4 (2 ng/ml) for 7 days. Additional media containing IL-4 (2 ng/ml) was added to the cultures on days 2 and 4. The B cells were then isolated and cultured on fresh NIH-3T3-CD154/BLyS cells with exogenous human IL-21 (10 ng/ml) for 5 days as indicated. The cells were then isolated, cultured with CpG+ PIB for 5 h and stained for cell surface CD19 and cytoplasmic IL-10 expression. Bar values represent mean (±SEM) $CD19^+$ B cell and B10 cell numbers, or B10 cell frequencies (solid line) from two independent experiments.

To determine whether IL-21 and CD40 signals drive human B10 cell expansion in vitro, purified blood B cells (1×10$^6$/ml) were cultured on confluent monolayers of mitomycin C-treated NIH-3T3 cells expressing the mouse T cell ligand for CD40 (mCD154) and human BLyS (hBLyS) in the presence of human IL-4 (2 ng/ml) for 7 days to induce B10pro cell maturation into IL-10-competent B10 cells. The B cells were then cultured on fresh NIH-3T3-mCD154/hBLyS cell monolayers with exogenous human IL-21 (10 ng/ml) for 5 days. NIH-3T3 cells expressing mouse CD154 were used for both the mouse and human studies because mouse CD154 binds human CD40 (Bossen et al. 2006 J. Biol. Chem. 281:13964-13971) and mouse CD154 can induce signals through both mouse and human CD40 (Armitage et al. 1992 Nature 357:80-82 and Yasui et al., 2002 Intl. Immunol. 14:319-329). By contrast, human CD154 does not bind mouse CD40 (Bossen et al., 2006). Human BLyS was used for both mouse and human B cell expansion because human BLyS appears to bind both human and mouse receptors (BCMA, TACI and BAFF-R) similarly (Bossen et al. 2006)). After the 12 day culture period, B cell numbers increased by 130 (±17)-fold, while B10 cell numbers were increased by 5-6,000-fold, with 13-16% of the B cells expressing IL-10 following 5 h of stimulation with phorbol ester, ionomycin and Brefeldin-A (FIG. 7). These results parallel our early results with in vitro expansion of mouse B cells and B10 effector cells, and indicate that this culture system is translatable to humans.

As occurred with our mouse studies, additional refinement of the culture system and protocols will be required for maximal human blood B cell and B10 effector cell expansion. These findings are not unanticipated as human 13 cell subpopulations respond differently to graded levels of CD40-CD154 interactions (Neron et. al. 2005 Immunology 116:454-463) and various forms of CD40 ligand used for in vitro stimulation of human B cells, such as membrane-associated CD154, soluble trimeric, dimeric or monomeric CD154 proteins or anti-CD40 antibodies, produce distinct functional responses in a wide range of B cell activities (Fanslow et al. 1994 Sem. Immunol. 6:267-278). Furthermore, human CD40 costimulation is differentially affected by cytokines. For example, CD40 ligation in the presence of IL-4 co-stimulates human B cells to secrete IgE and IgG4, while CD40 ligation in the presence of IL-2 or IL-10 induces human blood or tonsil B cells to secrete other Ig isotypes (IgM, IgG1, IgG2, IgG3 and IgA). Feeder cell supplemental factors involved in ex vivo B cell expansion. Our findings during in vitro expansion of mouse and human B cells and B10 effector cells demonstrate that this culture system is translatable to humans, but is not solely dependent on the addition of exogenous IL-4 and IL-21, or feeder cell expression of CD154 and BLyS. Each of these factors must be optimized for maximal B cell and B10 cell expansion and different B cell subpopulations respond differently to graded levels of CD40-CD154 interactions (Neron et al., 2005 Immunology 116:454-463). Furthermore, it is anticipated that additional factors can be added to the cultures or expressed by the feeder cells to further optimize B cell and B10 cell expansion.

Most important is that not all mouse NIH-3T3 (Swiss) fibroblasts, mouse 3T3-Balb/c fibroblasts, or human EA Hy.926 endothelial cells (Li et al., 1998 J. Exp. Med. 188:1385-1390 and Edgell et al., 1983 Proc. Natl. Acad. Sci., USA 80:3734-3737) are equivalent. For example, CD154$^+$BLyS$^+$ NIH-3T3 and 3T3-Balb/c fibroblasts were able to induce dramatic B cell activation and proliferation, with the majority of activated B cells adhering to the stromal cells and forming large grape-like clusters. By contrast, EA Hy.926 endothelial cells were only able to induce dramatic B cell activation and the activated B cells did not adhere to the stromal cells. However, we subsequently determined that EA Hy.926 cells did not express vascular cell adhesion molecule 1 (VCAM-1), while both fibroblast cell lines constitutively expressed VCAM-1 (Table 1; below). Importantly, we have determined that B cell adhesion to stromal cells is required for their initial activation and expansion in the culture system. VCAM-1 is critical for molecular interactions between stromal cells and B cell precursors that lead to B lymphohematopoiesis (Kincade et al., 1989 Annu. Rev. Immunol. 7:111-143 and Kincade 1992 Semin Immunol 3:379-390). Similarly, CD44 binding of hyaluronic acid and potentially other molecules is required for B cell adherence to bone marrow stromal cells and subsequent lymphohematopoiesis in long term bone marrow cultures (Lesley et al. 1992 *J. Exp. Med.* 175:257-266.). Both NIH-3T3 and 3T3-Balb/c fibroblasts constitutively express CD44 (Table 1). Thus, effective stromal cells must express appropriate cell surface molecules and/or provide an appropriate substrate for B cell attachment. Thereby, stromal cells for optimal B cell and B10 cell expansion would minimally express CD154, BLyS, VCAM-1 and CD44, or other functionally equivalent molecules, with exogenous IL-4 and IL-21 added or these cytokines produced by the stromal cells at optimized levels.

Transfected stromal cell cultures that were functionally selected for optimal CD154 and BLyS expression were able to support B cell expansion, but there was tremendous heterogeneity between different batch transfectants, individual clones, and their subclones despite similar CD154 and BLyS expression. The tremendous heterogeneity in abilities of different transfectants to support B cell expansion was eventually explained by our finding that there was extreme cellular and functional heterogeneity within each CD154$^+$BLyS$^+$ stromal cell population. Although unexpected, it is well recognized that stromal cells can express signaling molecules and secrete cytokines, can respond to some of those signaling molecules and cytokines themselves, can respond to exogenous cytokines added to the cultures, and that they can retain differentiation potential depending on their culture conditions.

Within our transfected stromal cell populations, we determined that only a subset of the cells were able to support robust B cell adhesion and clonal expansion, with a frequency that was commonly <1% of stromal cells despite all of the cells expressing CD154 and secreting BLyS. These stromal cell cultures were generally able to induce B cell expansion by <20-fold. However, mechanical isolation allowed us to isolate optimal cells that uniformly supported B cell expansion over a broad range up to 25,000-fold as described above (FIG. 4). Stromal cells optimized for maximal B cell and B10 cell growth can be mechanically isolated based on phenotypic, morphologic and growth characteristics. For example, it was possible to enrich for stromal cells that had a greater capacity to support B cell expansion by isolating individual stromal cells that supported B cell adhesion and rosette formation. Additional mechanical means for isolating optimal stromal cells for B cell expansion can include single cell-cloning techniques, flow cytometry isolation of cells based on their expression or loss of cell surface molecules, and/or other techniques known to those with skill in the art, with the subsequent functional identification of stromal cells that support optimal B cell expansion.

The bone marrow microenvironment and stromal cells can either positively or negatively influence whether a given B cell precursor or B cell proliferates, differentiates, or undergoes apoptosis. For example, several stromal cell lines that support lymphocyte outgrowth suppress the spontaneous apoptosis of pre-B cells by as much as 90%, while other stromal cell clones can induce lymphocyte apoptosis, or can appear inert. Borghesi et al. 1997 *J Immunol* 159:4171-4179. Similar observations have been made for the stromal cells used for B cell expansion in our studies. As examples, three representative clones expressing mouse CD154 and human BLyS are shown with one transfected clone from 3T3-Balb/c parental cells and two transfected clones (1 and 2) derived from parental NIH-3T3 cells (Table 1). At the time of these studies, clone #1 3T3-Balb/c cells supported optimal B cell expansion in comparison with clones 1 and 2 of NIH-3T3 cell origin, which were relatively less effective. Microarray analysis of these three clones in comparison with their parental 3T3 cells demonstrated considerable molecular heterogeneity between the cells cultured under identical conditions. The expression of some molecules was either upregulated or down-regulated, which correlated with optimal B cell expansion. However, the level of molecular heterogeneity between sub-clones was the most unexpected finding. Examples of the molecular differences that are likely to be functional are illustrated below.

Molecules that were upregulated in 3T3 cells with the potential to significantly expand B cells included CD24, also known as heat-stable antigen in the mouse. CD24 is a glycosylphosphatidylinositol-anchored membrane protein of heterogeneous molecular weight ranging from 30 to 70 kDa. The mature protein is only 27 to 30 amino acids long, and most of the molecular weight of the protein consists of extensive N- and O-linked glycosylation. CD24 is expressed by B cells and their precursors and neutrophils, in neuronal tissue, and in certain epithelial cells. CD24 functions as a mucin-like adhesion molecule that can facilitate and regulate cell-cell interactions. Increased stromal cell IL-7 expression by clone #1 3T3-Balb/c cells may be critical to B10 and B cell expansion. IL-7 is normally made at extremely small levels by stromal cells, but it is an essential stimulus for early B cell precursor replication, and other critical developmental functions. Clone #1 3T3-Balb/c cells also expressed Macrophage stimulating 1 (Mst1), also known as Step 20-like kinase or STK4 (serine threonine kinase 4), the human ortholog of *Drosophila* Hippo. STK4 is a central caspase 3-activated constituent of a highly conserved pathway controlling cell growth and apoptosis. Importantly, lymphocytes and neutrophils from STK4-deficient mice exhibit enhanced loss of mitochondrial membrane potential and increased susceptibility to apoptosis. Mst1 also has crucial roles in lymphocyte adhesion to endothelial cells during lymphocyte trafficking in vivo and Mst1$^{-/-}$ mice have hypotrophic peripheral lymphoid tissues and reduced marginal zone B cells in the spleen. Thymic stromal lymphopoietin (Tslp) protein is primarily produced by certain stromal cells and fibroblasts and acts on myeloid lineage cells to produce factors that influence T cell lineage development and certain T cell subsets including regulatory T cells. TSLP may also support B cell differentiation from fetal hematopoietic progenitors. TSLP is proposed to signal through a heterodimeric receptor complex composed of the TSLP receptor and the IL-7Rα chain, suggesting that TSLP and IL-7 may influence some signaling pathways in common.

Multiple stromal cell molecules are likely to negatively influence B cell proliferation, differentiation, and interactions with stromal cells, or induce their apoptosis. CD99 is expressed by endothelial cells as well as most leukocytes, including B cells. CD99 functions as an adhesion molecule, and also interacts with the intracellular molecule cyclophylin A that is intricately involved in inflammatory signaling pathways. Homotypic CD99-CD99 interactions have been shown between monocytes and endothelial cells during diapedesis. CD99 signaling may be detrimental to B cell expansion as CD99 ligation on early B cells using an anti-CD99 monoclonal antibody induces apoptosis. Likewise, CD99 signaling induces the apoptosis of developing T cells in the thymus. Interactions between the mouse homologue of CD99 (designated D4) and its ligand, paired immunoglobulin-like type 2 receptor (PILR) widely expressed by leukocytes, is a major mechanism inducing thymocyte apoptosis.

As a second example, transforming growth factor beta-induced (Tgthbi) expression was down-regulated by both clone #1 3T3-Balb/c cells and clone #1 NIH-3T3 cells in comparison with their parental cells. Transforming growth factor beta-induced (TGFBI) protein is a secreted RGD-containing protein induced by transforming growth factor-beta that binds to type I, II and IV collagens and may thereby inhibit cell adhesion. ROD motifs are found in many extra-cellular matrix proteins that modulate cell adhesion and the motif serves as a ligand recognition sequence for several integrins during cell-collagen interactions. TGFBI can inhibit adhesive interactions regulating the invasive growth of melanoma cells. The loss of TGFBI expression has been implicated in cell proliferation, tumor progression, and angiogenesis.

In a third example, stromal cell CXCR7 transcripts were down-regulated in both clone #1 3T3-Balb/c cells and clone #1 NIH-3T3 cells. CXCR7 (formerly RDC1) functions as a receptor for the CXCL12 (formerly SDF-1) chemokine that binds B cells and can regulate a spectrum of normal and pathological processes. CXCR7 can function as a scavenger receptor for CXCL12 that is also normally produced by both parental 3T3 cell lines. Thereby, stromal cell loss of CXCR7 expression may facilitate CXCL12 binding to B cells in the culture system.

Cell surface differentiation-regulating proteins may also be counterproductive to optimal B cell expansion. Delta-like 1 and Jagged 1 expression and their shared receptor Notch 1 were down-regulated on clone #1 3T3-Balb/c cells in comparison with untransfected parental cells. Notch, Delta-like and Jagged proteins play pivotal roles in B cell development and activation. For example, Notch-1 engagement on B cells by Delta-like 1 expressed on stromal cells promotes B cell differentiation into antibody-secreting cells, while Notch-1 interactions with Jagged-1 are inhibitory in this process. Also, Notch-Delta-like 1 interactions act in synergy with B cell antigen receptor and CD40 signaling to enhance B cell proliferation and isotype switching. In addition, marginal zone B cell development critically requires Delta-like 1 interactions with B cell-expressed Notch-2. Other aspects of 13 cell development are negatively regulated by Notch/Delta-like/Jagged interactions. For example, 3T3 fibroblasts expressing Delta-like 1 have been reported to act as stromal cells for adipocyte differentiation, but only support early B cell differentiation when Delta-like expression is suppressed or if interleukin-7 (IL-7) is also provided to the cultures. Therefore, the role of the Notch/Delta-like/Jagged axis in the development and function of 110 cells may be complex, but these proteins may be critical regulators of B cell and B10 cell expansion.

Stromal cells for maximal B cell and B10 cell expansion may thereby optimally express appropriate densities of CD154, BLyS, VCAM-1 and CD44, or other functionally equivalent molecules, along with optimal expression of some or all of the molecules outlined in Table 1 in combination with exogenous IL-4 and IL-21 added to the cultures. As each of the molecules that influence B cell and B10 cell expansion are better defined, it will be critical to evaluate the function of each molecule in combination with other factors endogenously expressed by the stromal cells and exogenous stimuli added to the cultures. The cumulative effects of these positive and negative regulators will also depend on the timing in which these signals are presented during B cell and B10 cell expansion. Thereby, a functional definition of optimal stromal cells for B cell and B10 cell expansion is currently more operable than a molecular definition that includes all factors and pathways that are required to maximal B cell and B10 cell expansion.

TABLE 1

Transcripts expressed by stromal cells optimized for B cell and B10 cell expansion.

| Gene Symbol | Gene Title | Fold-Change | 3T3-Balb/c Clone 1 | 3T3-Balb/c Parent | NIH 3T3-Swiss clone 1 | NIH 3T3-Swiss clone 2 | NIH 3T3-Swiss Parent |
|---|---|---|---|---|---|---|---|
| | Relative capacity for B10 cell expansion | | ++++ | − | ++ | + | − |
| | Upregulated | | | | | | |
| Cd24a | CD24a antigen | 10.13 | 3197 | 439 | 647 | 238 | 147 |
| Cd24a | CD24a antigen | 6.05 | 5318 | 1317 | 1814 | 676 | 370 |
| Cd24a | CD24a antigen | 4.12 | 960 | 336 | 439 | 181 | 111 |
| Il7 | interleukin 7 | 20.19 | 647 | 83 | 24 | 24 | 23 |
| Il7 | interleukin 7 | 3.66 | 67 | 17 | 24 | 17 | 17 |
| Mst1 | macrophage stimulating 1 | 4.90 | 208 | 48 | 46 | 37 | 39 |
| Tslp | thymic stromal lymphopoietin | 1.23 | 82 | 20 | 355 | 74 | 38 |
| | Downreg: | | | | | | |
| Cd99 | CD99 antigen | −9.26 | 67 | 682 | 902 | 545 | 448 |
| Cd99 | CD99 antigen | −9.43 | 65 | 631 | 892 | 529 | 481 |
| Cd99 | CD99 antigen | −22.14 | 35 | 899 | 1244 | 670 | 508 |
| Cxcr7 | chemokine (C-X-C motif) receptor 7 | −73.82 | 12 | 1684 | 55 | 2445 | 2543 |
| Dlk1 | delta-like 1 homolog (*Drosophila*) | −4.31 | 56 | 750 | 201 | 227 | 96 |
| Dlk1 | delta-like 1 homolog (*Drosophila*) | −89.03 | 59 | 11502 | 8915 | 6262 | 1191 |
| Jag1 | jagged 1 | −2.37 | 43 | 98 | 358 | 57 | 54 |
| Jag1 | jagged 1 | −11.34 | 29 | 493 | 1755 | 103 | 128 |
| Jag1 | jagged 1 | −53.26 | 18 | 2094 | 5614 | 149 | 434 |
| Notch1 | Notch gene homolog 1 (*Drosophila*) | −12.74 | 50 | 599 | 754 | 661 | 547 |
| Notch1 | Notch gene homolog 1 (*Drosophila*) | −4.01 | 68 | 242 | 318 | 265 | 272 |
| Tgfbi | transforming growth factor, beta induced | −14.43 | 13 | 192 | 19 | 586 | 570 |
| Tgfbi | transforming growth factor, beta induced | −14.62 | 16 | 182 | 26 | 785 | 772 |
| Tgfbi | transforming growth factor, beta induced | −36.28 | 11 | 539 | 11 | 2062 | 2196 |

TABLE 1-continued

Transcripts expressed by stromal cells optimized for B cell and B10 cell expansion.

| Gene Symbol | Gene Title | Fold-Change | 3T3-Balb/c Clone 1 | 3T3-Balb/c Parent | NIH 3T3-Swiss clone 1 | clone 2 | Parent |
|---|---|---|---|---|---|---|---|
| Tgfbi | transforming growth factor, beta induced | −9.38 | 46 | 395 | 30 | 1815 | 1663 |
| Constitutive: | | | | | | | |
| Cd44 | CD44 antigen | 1.30 | 416 | 688 | 123 | 308 | 403 |
| Cd44 | CD44 antigen | −1.41 | 2061 | 5511 | 1508 | 2911 | 2937 |
| Cd44 | CD44 antigen | −2.12 | 1826 | 5671 | 2410 | 4120 | 3991 |
| Vcam1 | vascular cell adhesion molecule 1 | −1.94 | 193 | 326 | 1496 | 224 | 179 |
| Vcam1 | vascular cell adhesion molecule 1 | −2.16 | 132 | 347 | 778 | 152 | 162 |
| Vcam1 | vascular cell adhesion molecule 1 | −2.43 | 396 | 803 | 5015 | 545 | 388 |
| Vcam1 | vascular cell adhesion molecule 1 | −2.43 | 396 | 803 | 5015 | 545 | 388 |

Total RNA was extracted from parental 3T3 cells and their cDNA-transfected subclones using TRIzol (Invitrogen-Molecular Probes), with relative transcript levels quantified in parallel by GeneChip analysis (Affymetrix Mouse Genome 430 2.0 GeneChips; Affymetrix, Santa Clara, CA). All quality parameters for the arrays were confirmed to be in the range recommended by the manufacturer. Linear relative expression levels are shown for each line. The results for reiterative probes on each gene chip are shown.

Methods

Mice.

C57BL/6, IL-10$^{-/-}$ (B6.129P2-Il10$^{tm1Cgn}$/J) (Kuhn, et al., Interleukin-10-deficient mice develop chronic enterocolitis. Cell 75, 263-274 (1993)), CD40$^{-/-}$ (B6.129P2-CD40$^{ml/Kik}$/J), and MD4 (C57BL/6-Tg(TghelMD4)4Ccg/J) mice were from the Jackson Laboratory (Bar Harbor, Me.). MHC-II$^{-/-}$ (B6.129-H2-Ab1$^{tm1Jae}$B2m$^{tmGru}$N17) mice (Taconic Farms, Inc., Hudson, N.Y.) were as described (Grusby, M. J. et al. Mice lacking major histocompatibility complex class I and class II molecules. Proc. Natl. Acad. Sci. USA 90, 3913-3917 (1993)). CD19$^{-/-}$ mice were backcrossed onto the C57BL/6 background for 14 generations. See Sato, S., Ono, N., Steeber, D. A., Pisetsky, D. S. & Tedder, T. F. CD19 regulates B lymphocyte signaling thresholds critical for the development of B-1 lineage cells and autoimmunity. J. Immunol. 157, 4371-4378 (1996) and Sato, S., Steeber, D. A., Jansen, P. J. & Tedder, T. F. CD19 expression levels regulate B lymphocyte development: human C19 restores normal function in mice lacking endogenous CD19. J. Immunol. 158, 4662-4669 (1997). IL-21R$^{-/-}$ mice were as described. See Ozaki, K. et al. A critical role for IL-21 in regulating immunoglobulin production. Science 298, 1630-1634 (2002). TCR$^{MOG}$ transgenic mice ((Bettelli, E. et al. Myelin oligodendrocyte glycoprotein-specific T cell receptor transgenic mice develop spontaneous autoimmune optic neuritis. J. Exp. Med. 197, 1073-1081 (2003)) Thy1.2$^+$, provided by Dr. V. K. Kuchroo, Harvard Medical School, Boston, Mass.) were crossed to C57BL/6.Thy1.1 mice to generate Thy1.1-expressing T cells. All mice were bred in a specific pathogen-free barrier facility and used at 6-12 wks of age. The Duke University Animal Care and Use Committee approved all studies.

Cell Preparation.

Single-cell suspensions from spleens and peripheral lymph nodes (paired axillary and inguinal) were generated by gentle dissection, with the cells passed through 70-mm cell strainers (BD Biosciences, San Diego, Calif.) followed by percoll gradient (70/37%) centrifugation. Lymphocytes were collected from the 37:70% interface and washed. MACS (Miltenyi Biotech, Auburn, Calif.) was used to purify lymphocyte populations according to the manufacturer's instructions. CD19 mAb-coated microbeads and CD4$^+$ T cell isolation kits (Miltenyi Biotech) were used to purify B cells and CD4$^+$ T cells, respectively. When necessary, the cells were enriched a second time using a fresh MACS column to obtain >95% cell purities.

Immunofluorescence Analysis.

FITC-, PE-, PE-Cy5-, PE-Cy7-, or APC-conjugated CD1d (1B1), CD4 (H129.19), CD5 (53-7.3), CD19 (1D3), B220 (RA3-6B2), and Thy1.1 (OX-7) mAbs were from BD Biosciences. PE-conjugated IL-21R (4A9) mAb was from BioLegend (San Diego, Calif.). Intracellular staining used mAbs reactive with IL-10 (JES5-16E3), IL-17 (17B7), and IFN-γ (XMG1.2) (all from eBioscience) and Cytofix/Cytoperm kits (BD Biosciences). Background staining was assessed using non-reactive, isotype-matched control mAbs (Caltag Laboratories, San Francisco, Calif.). For two- to six-color immunofluorescence analysis, single cell suspensions ($10^6$ cells) were stained at 4° C. using predetermined optimal mAb concentrations for 20 min as described. See Yanaba et al. 2008, Immunity 28, 639-650; Matsushita et al. 2008, J. Clin. Invest. 118, 3420-3430; Matsushita et al. 2010, J. Immunol. 185, 2240-2252; Matsushita and Tedder 2011, Methods Mol. Biol. 677, 99-111; and Zhou et al. 1994, Mol. Cell. Biol. 14, 3884-3894. Blood erythrocytes were lysed after staining using FACS™ Lysing Solution (Becton Dickinson, San Jose, Calif.).

B cell intracellular IL-10 expression was visualized by immunofluorescence staining and analyzed by flow cytometry as described. See Yanaba et al. 2008, Immunity 28, 639-650 and Matsushita and Tedder 2011, Methods Mol. Biol. 677, 99-111. Briefly, isolated leukocytes or purified cells were resuspended ($2 \times 10^6$ cells/ml) in complete medium (RPMI 1640 media containing 10% FCS, 200 µg/ml penicillin, 200 U/ml streptomycin, 4 mM L-Glutamine, and $5 \times 10^{-5}$ M 2-mercaptoethanol, all from Gibco. Carlsbad, Calif.) with LPS (10 µg/ml, Escherichia coli serotype 0111: B4, Sigma), PMA (50 ng/ml; Sigma), ionomycin (500 ng/ml; Sigma) and monensin (2 µM; eBioscience) for 5 h in 48-well flat-bottom plates. In some experiments, the cells were incubated for 48 h with an agonistic anti-mouse CD40 mAb (1 µg/ml; HM40-3 mAb; BD Pharmingen) as described. Yanaba et al. 2009, J. Immunol. 182, 7459-7472. For IL-10 detection, Fc receptors were blocked with mouse Fc receptor mAb (2.4G2; BD PharMingen), and dead cells were detected using a LIVE/DEAD® Fixable Violet Dead Cell Stain Kit (Invitrogen-Molecular Probes) before cell surface staining. Stained cells were fixed and permeabilized using a Cytofix/Cytoperm kit (BD PharMingen) according to the manufacturer's instructions and stained with PE-conjugated mouse anti-IL-10 mAb.

Splenocytes from IL-10$^{-/-}$ mice served as negative controls to demonstrate specificity and to establish background IL-10 staining levels. For T cell intracellular cytokine staining, lymphocytes were stimulated in vitro with PMA (50 ng/ml; Sigma, St. Louis, Mo.) and ionomycin (1 µg/ml; Sigma) in the presence of Brefeldin A (BFA, 1 µl/ml; eBioscience) for 5 h before staining. Viable cells with the forward and side light scatter properties of lymphocytes were analyzed using a FACScan flow cytometer (Becton Dickinson) or BD FACSCanto™ II (BD Biosciences).

In Vitro B Cell Cultures.

Purified splenic B cells (1×10$^6$/ml) were cultured in RPMI 1640 medium containing 10% FBS, 2 mM L-Glutamine, penicillin (100 I.U./ml), streptomycin (100 µg/ml), and 50 µM 2-mercapthoethanol, and either recombinant IFN-γ (10 ng/ml IL-4 (2 ng/ml), IL-6 (10 ng/ml) or IL-21 (100 ng/ml) (from e-Bioscience); TGF-β (10 ng/ml). IL-10 (10 ng/ml), or IL-12 (10 ng/ml) (from R&D systems, Minneapolis, Minn.); or IL-23 (20 ng/ml) and IL-27 (100 ng/ml) (Biolegend), or LPS (10 µg/ml) before B10 cell numbers and culture supernatant fluid IL-10 concentrations were determined. IL-10 concentrations were determined by ELISA. In separate experiments, purified spleen B cells were cultured with NIH-3T3 cells expressing CD154 and BLyS as described with exogenous recombinant IL-4 (2 ng/ml) or IL-21 (10 ng/ml) added to the cultures. Nojima et al. 2011, Nature Comm. 2, 465 and Tedder et al. in Leukocyte Typing V: White Cell Differentiation Antigens. Vol. 1 (eds S. F. Schlossman et al.) 483-504 (Oxford University Press, 1995). For adoptive transfer experiments, cultured CD5$^+$ and CD5$^+$ B cells were purified by cell sorting (FACSVantage SE, Becton Dickinson), with purities of 95-98%. After purification, 1×10$^6$ cells were immediately transferred i.v. into each recipient mouse. In some experiments, CD40 mAb (clone HM40-3; hamster, no azide/endotoxin-free, BD Pharmingen, San Jose, Calif.) was added to cultures where indicated.

EAE Induction.

EAE was induced in 6- to 8-week-old female mice by subcutaneous immunization with 100 µg of MOG$_{35-55}$ peptide (MEVGWYRSPFSRVVHLYRNGK; NeoMPS, San Diego, Calif.) emulsified in CFA containing 200 µg of heat-killed *Mycobacterium tuberculosis* H37RA (Difco, Detroit, Mich.) on day 0. See Matsushita et al. 2008, J. Clin. Invest. 118, 3420-3430 and Matsushita et al. 2010, J. Immunol. 185, 2240-2252. Additionally, mice received 200 ng of pertussis toxin (List Biological Laboratories, Campbell, Calif.) i.p. in 0.5 ml of PBS on days 0 and 2. Clinical signs of disease were assessed daily with a 0 to 6 point scoring system: 0, normal; 1, flaccid tail; 2, impaired righting reflex and/or gait; 3, partial hind limb paralysis; 4, total hind limb paralysis; 5, hind limb paralysis with partial forelimb paralysis; 6, moribund state, as described. Fillatreau et al. 2002, Nat. Immunol. 3, 944-950. Moribund mice were given disease severity scores of 6 and euthanized.

Adoptive Transfer Experiments.

B cells from naïve mice or mice with EAE (day 28) were first enriched using CD19 mAb-coated microbeads, stained for cell surface CD19, CD1d and CD5 expression, with CD1d$^{hi}$CD5$^+$ and CD1d$^{lo}$CD5$^-$ cells purified by cell sorting as described with purities of 95-98%. See Matsushita 2011, Methods Mol. Biol. 677, 99-111 and Yanaba et al. 2008, Immunity 28, 639-650. After purification, the CD1d$^{hi}$CD5$^+$ or CD1d$^{lo}$CD5$^-$ B cells (1×10$^6$) were immediately transferred i.v. into recipient mice, with 1B10 cells representing 13-20% and <0.1% of the transferred cells. In some experiments, donor Thy1.1 CD4$^+$ T cells were isolated from pooled spleens and lymph nodes of TCR$^{MOG}$ transgenic mice, then labeled with CFSE Vybrant™ CFDA SE fluorescent dye (5 µM; CFSE; Invitrogen) and transferred i.v. (5×10$^6$/mouse) into Thy1.2 congenic recipients. Five days after adoptive transfer, the TCR$^{MOG}$ CD4$^+$ T cells were assessed by flow cytometry.

Statistical Analysis.

All data are shown as means (±SEM). The significance of differences between sample means was determined using the Student's test.

We claim:

1. A method of expanding B10 cells capable of producing IL-10 ex vivo comprising culturing polyclonal B cells harvested from a subject with IL-21 and feeder cells expressing a CD40 agonist and a B cell survival promoter and isolating the polyclonal B10 cells.

2. The method of claim 1, further comprising first culturing the B cells on feeder cells expressing a CD40 agonist and BAFF (BLyS) in the presence of IL-4.

3. A method of expanding B cells ex vivo comprising:
   a) Culturing polyclonal B cells harvested from a subject on feeder cells expressing a CD40 agonist and a B cell survival promoter in the presence of IL-4;
   b) Culturing the B cells from step (a) on feeder cells expressing a CD40 agonist and a B cell survival promoter in the presence of IL-21;
   c) Isolating the B cells from step (b); and
   d) Isolating the polyclonal B10 cells from the B cells of step (c).

4. The method of claim 3, wherein the feeder cells further express at least one of VCAM-1, CD24, IL-7, Mst1, Tslp and CD44.

5. The method of claim 3, wherein the feeder cells express at least two fold less of CD99, CXCR7, Dlk1, Jag1, Notch1 or TGFBI than control feeder cells.

6. The method of claim 3, wherein the B cells are harvested from the blood, spleen, peritoneal cavity, lymph nodes, bone marrow, site of autoimmune disease, site of inflammation or tissue undergoing transplant rejection of the subject.

7. The method of claim 3, wherein the B cells are isolated by removal of non-B cells and selection for cell surface immunoglobulin (IgM, IgD, IgA, or IgE) prior to use in the method.

8. The method of claim 3, wherein the CD40 agonist is CD154, a fragment of CD154, or antibody, aptamer or polypeptide, or fragment thereof reactive with CD40.

9. The method of claim 3, wherein the B cell survival promoter is selected from at least one of feeder cells, BAFF (BLyS), BAFF fragments, APRIL, CD22 ligand, CD22 monoclonal antibody, or fragments thereof.

10. The method of claim 3, wherein the feeder cells are fibroblast, endothelial cells, epithelial cells, keratinocytes, melanocytes, or other mesenchymal or stromal cells.

11. The method of claim 3, wherein the culturing step with IL-4 is a three to ten day culture period and the culturing step with IL-21 is a four to eight day culture period.

12. The method of claim 3, wherein the isolated B10 cells are more than 50% B10 cells capable of producing IL-10.

13. The method of claim 3, wherein the number of B10 cells is expanded by at least 5,000 fold relative to the number of B cells harvested from the subject.

14. The method of claim 1, wherein the B10 cells are isolated by selecting for cells expressing a cell surface marker selected from the group consisting of CD1d, CD5, CD24, CD27 and combinations thereof.

15. The method of claim 3, wherein the B10 cells are isolated by selecting for cells expressing a cell surface marker selected from the group consisting of CD1d, CD5, CD24, CD27 and combinations thereof.

16. The method of claim 1, wherein the B cells used in the method represent the total B cells.

17. The method of claim 3, wherein the B cells used in the method represent the total B cells.

18. The method of claim 1, wherein the B cells are isolated by removal of non-B cells and selection for cell surface IgM prior to use in the method.

* * * * *